(12) United States Patent
Asai

(10) Patent No.: US 7,031,511 B2
(45) Date of Patent: Apr. 18, 2006

(54) HOLE INSPECTION APPARATUS AND METHOD

(75) Inventor: Norio Asai, Kyoto (JP)

(73) Assignee: Dainippon Screen Mfg. Co., Ltd., (JP)

( * ) Notice: Subject to any disclaimer, the term of this patent is extended or adjusted under 35 U.S.C. 154(b) by 682 days.

(21) Appl. No.: 10/159,758

(22) Filed: May 30, 2002

(65) Prior Publication Data

US 2002/0181760 A1  Dec. 5, 2002

(30) Foreign Application Priority Data

Jun. 1, 2001 (JP) ............................. 2001-166551

(51) Int. Cl.
   *G06K 9/00* (2006.01)
(52) U.S. Cl. ....................... 382/149; 382/282; 382/286; 382/190; 348/126
(58) Field of Classification Search ................ 382/141, 382/145, 147, 149, 151, 218, 282, 286, 293, 382/318, 325, 190, 194, 204, 205, 209; 348/126; 356/237.4, 237.5; 700/96, 116; 438/16
   See application file for complete search history.

(56) References Cited

U.S. PATENT DOCUMENTS

| | | | | |
|---|---|---|---|---|
| 4,555,798 A | * | 11/1985 | Broadbent et al. | 382/144 |
| 4,783,826 A | * | 11/1988 | Koso | 382/147 |
| 4,794,647 A | * | 12/1988 | Forgues et al. | 382/147 |
| 4,797,939 A | * | 1/1989 | Hoki et al. | 382/149 |
| 4,803,734 A | * | 2/1989 | Onishi et al. | 382/115 |
| 4,893,346 A | * | 1/1990 | Bishop | 382/147 |
| 5,146,509 A | * | 9/1992 | Hara et al. | 382/149 |
| 5,608,816 A | * | 3/1997 | Kawahara et al. | 382/149 |
| 5,774,574 A | * | 6/1998 | Hoki | 382/149 |
| 6,122,401 A | * | 9/2000 | Nagao | 382/216 |
| 6,330,354 B1 | * | 12/2001 | Companion et al. | 382/150 |

OTHER PUBLICATIONS

Moganti, Madhav, et al., "Automatic PCB Inspection Algorthms: A Survey," Computer Vision and Image Understanding, vol. 63, No. 2, pp. 287-313, Mar. 1996.*

* cited by examiner

*Primary Examiner*—Bhavesh M. Mehta
*Assistant Examiner*—John B. Strege
(74) *Attorney, Agent, or Firm*—Ostrolenk, Faber, Gerb & Soffen, LLP

(57) ABSTRACT

A defect candidate area extraction part determines whether or not each object pattern divisional area obtained by dividing picked-up image data of a printed board having through holes (holes) has a different portion exceeding a prescribed allowance between the same and a positionally corresponding area of a master pattern thereby determining whether or not each object pattern divisional area is a defect candidate and extracting a defect candidate area. Further, a defect determination part determines whether or not each through hole is defective on the basis of a result of comparison between hole information as to the through hole present in the object pattern divisional area extracted from the plurality of object pattern divisional areas as the defect candidate area and hole information as to a through hole present in an area of the master pattern corresponding to the defect candidate area. Thus provided is a hole inspection apparatus capable of correctly and efficiently inspecting holes.

20 Claims, 17 Drawing Sheets

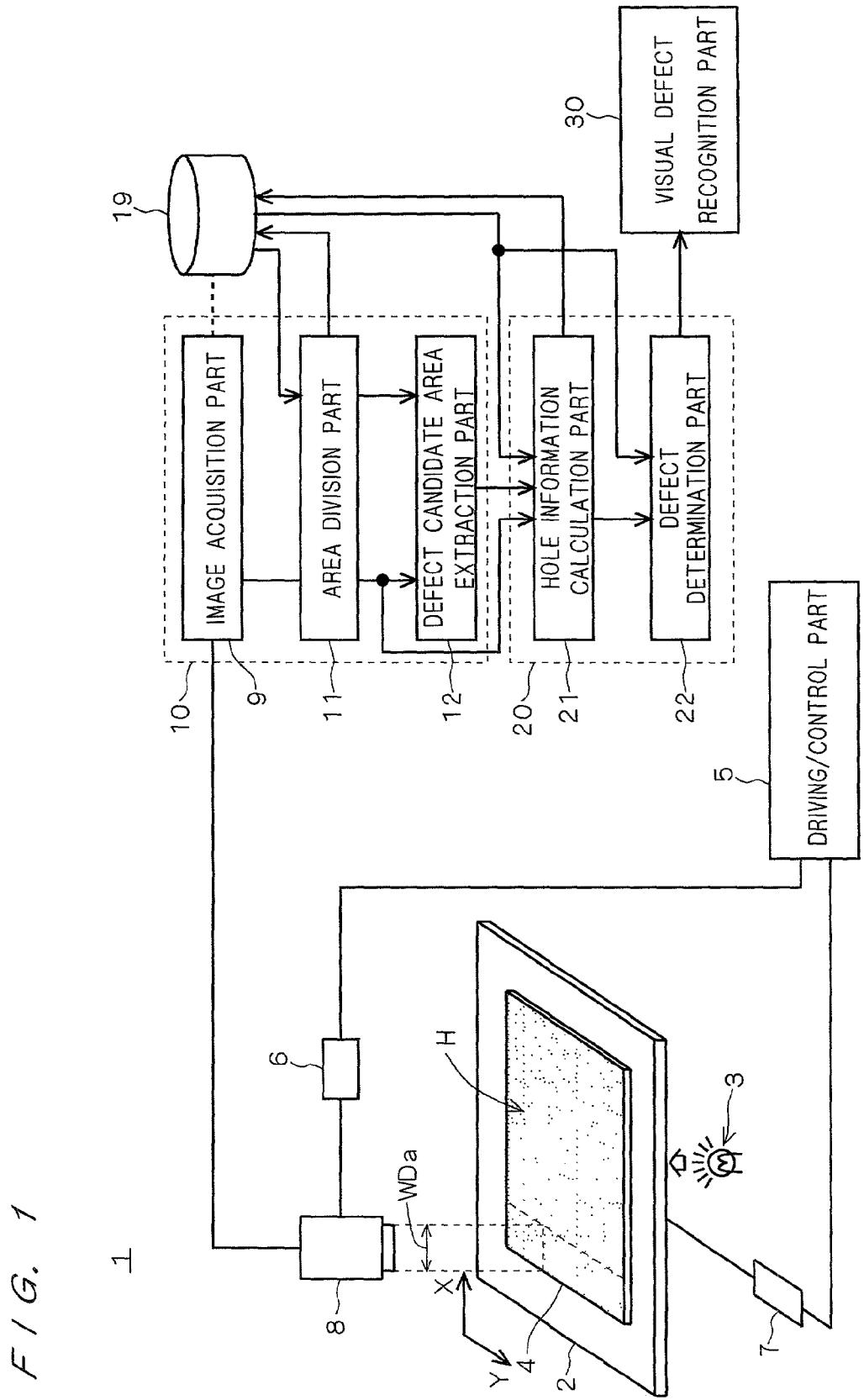

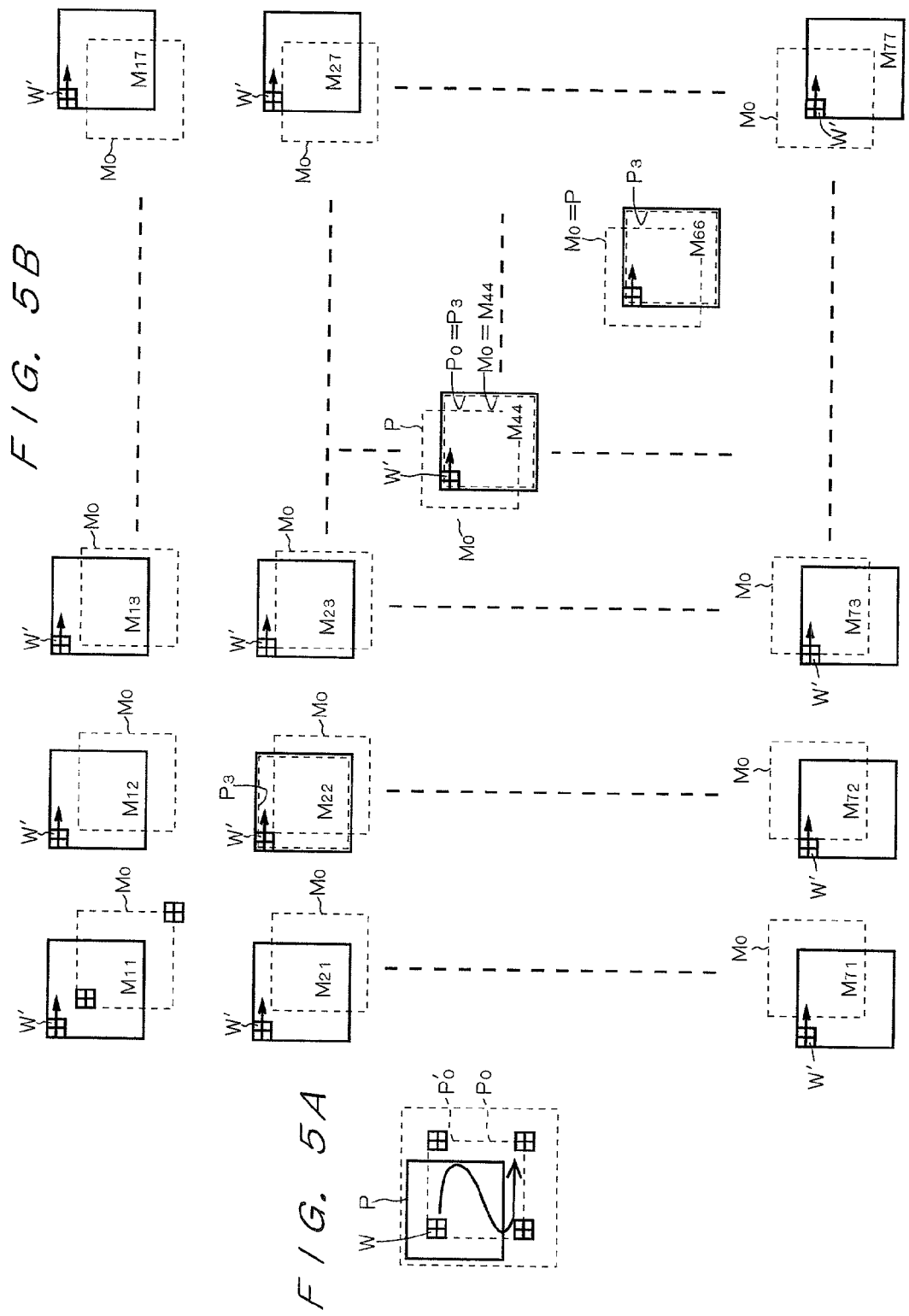

F I G. 7A
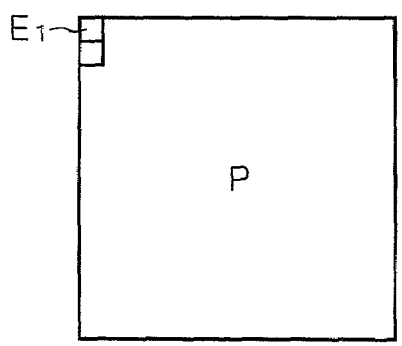
F I G. 7B
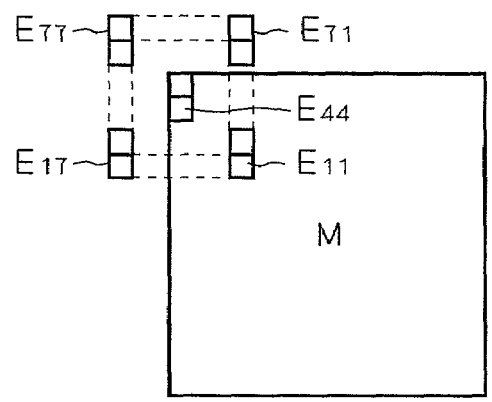

FIG. 9

F I G. 13
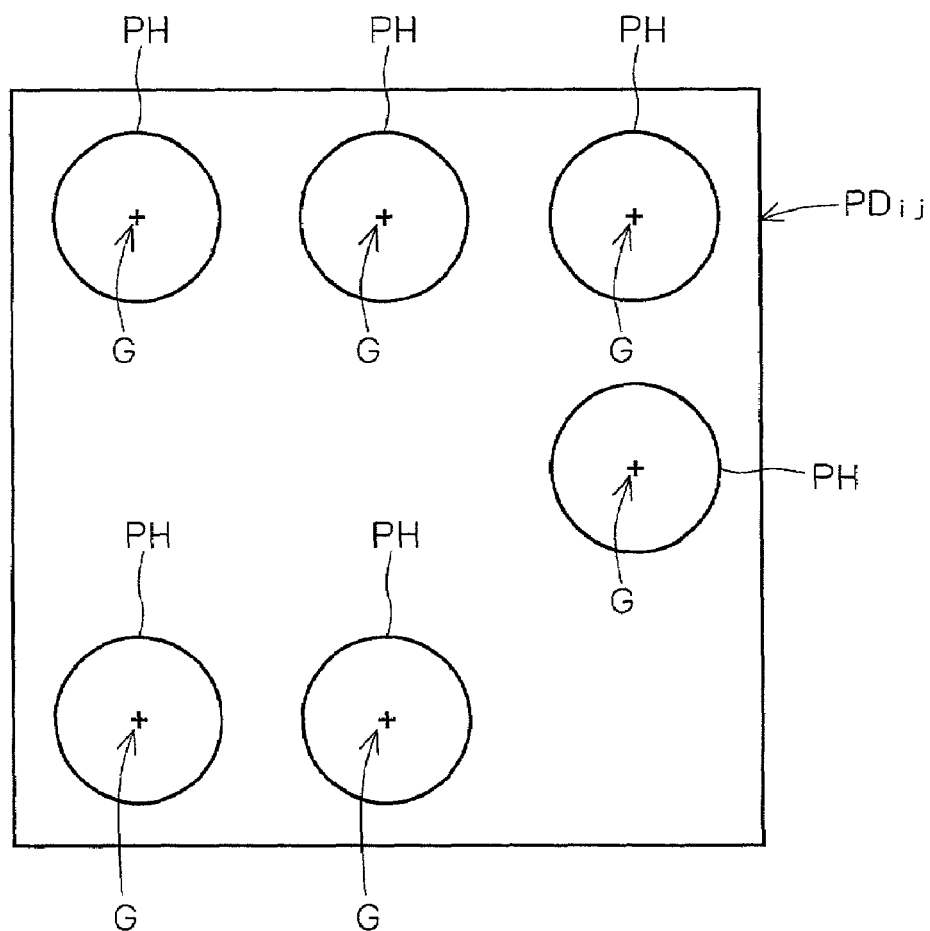

F I G. 1 4
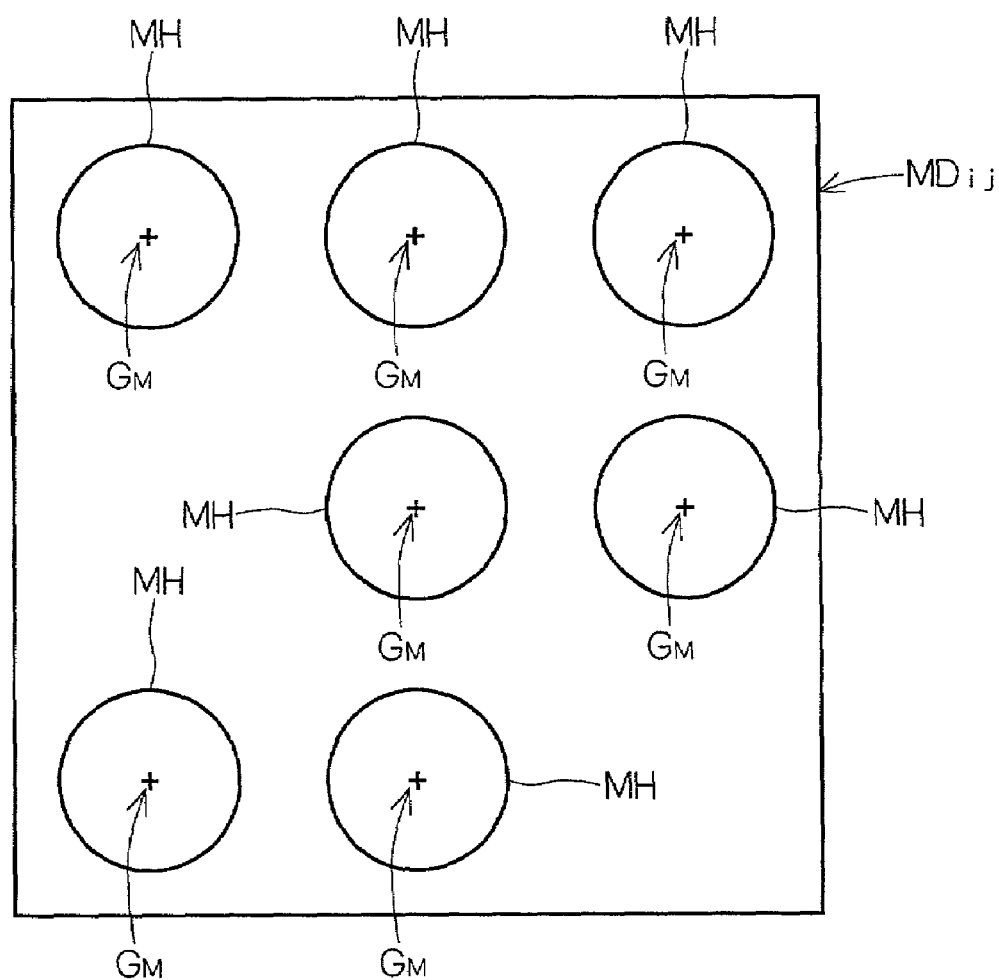

F I G. 15
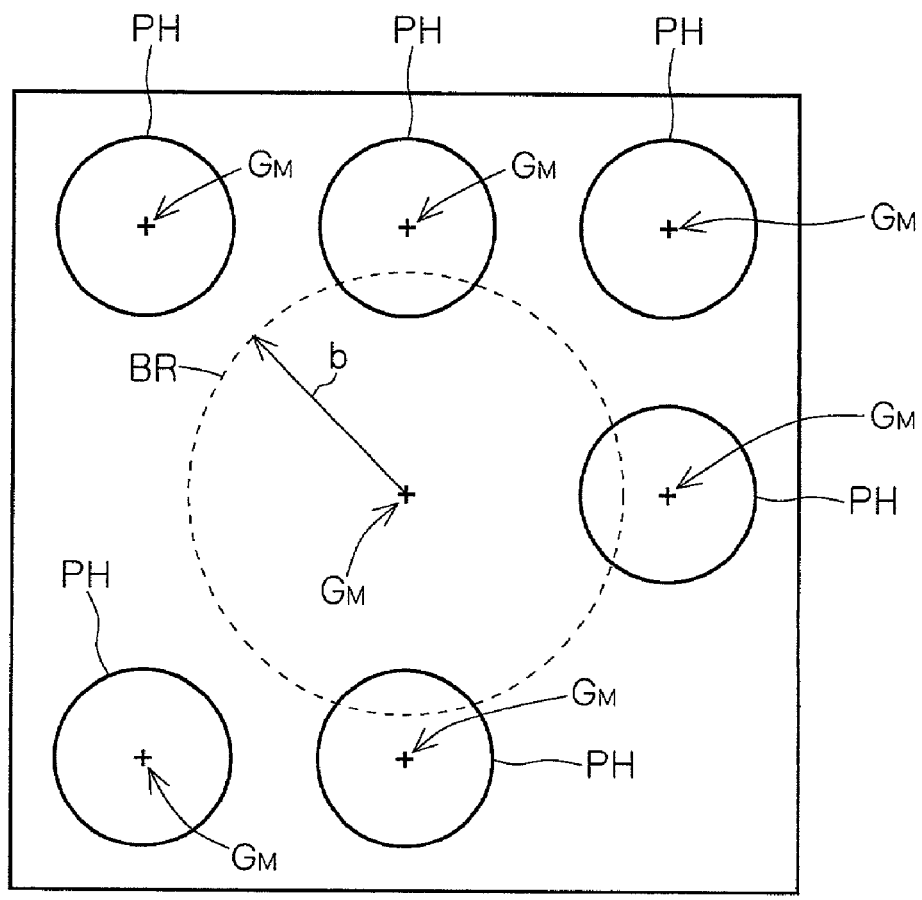

F I G. 16
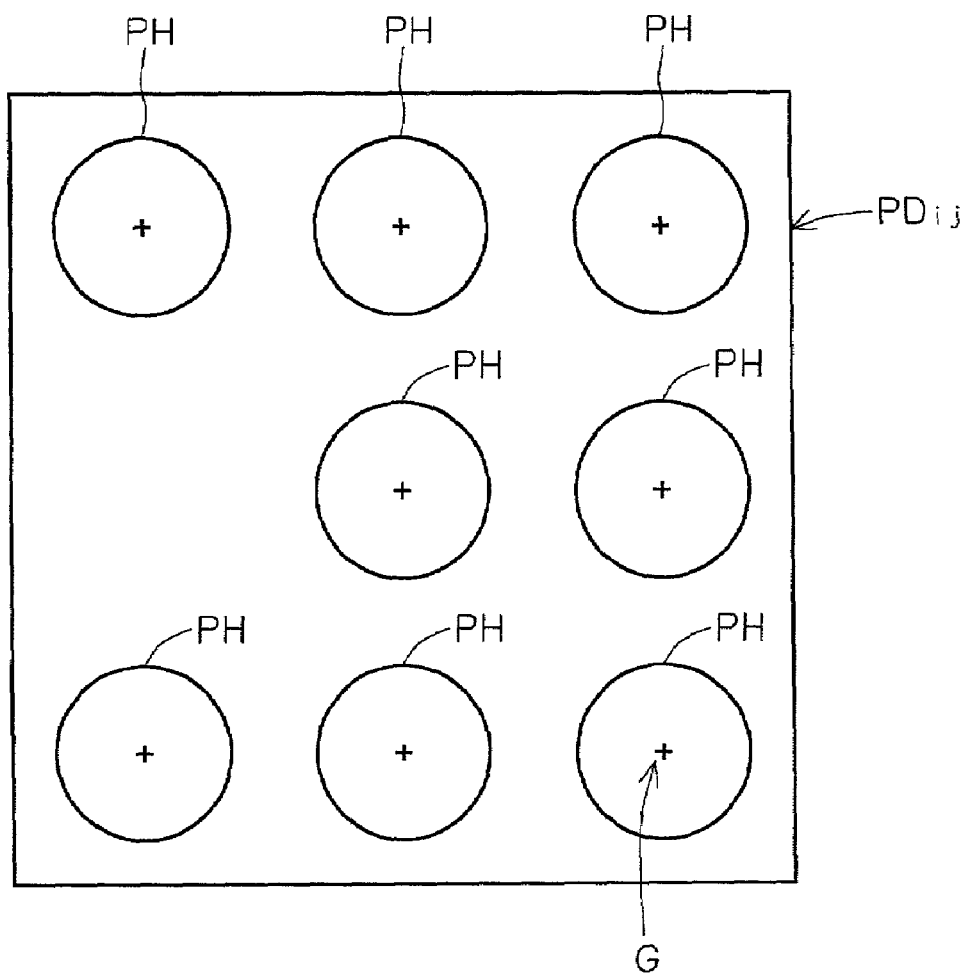

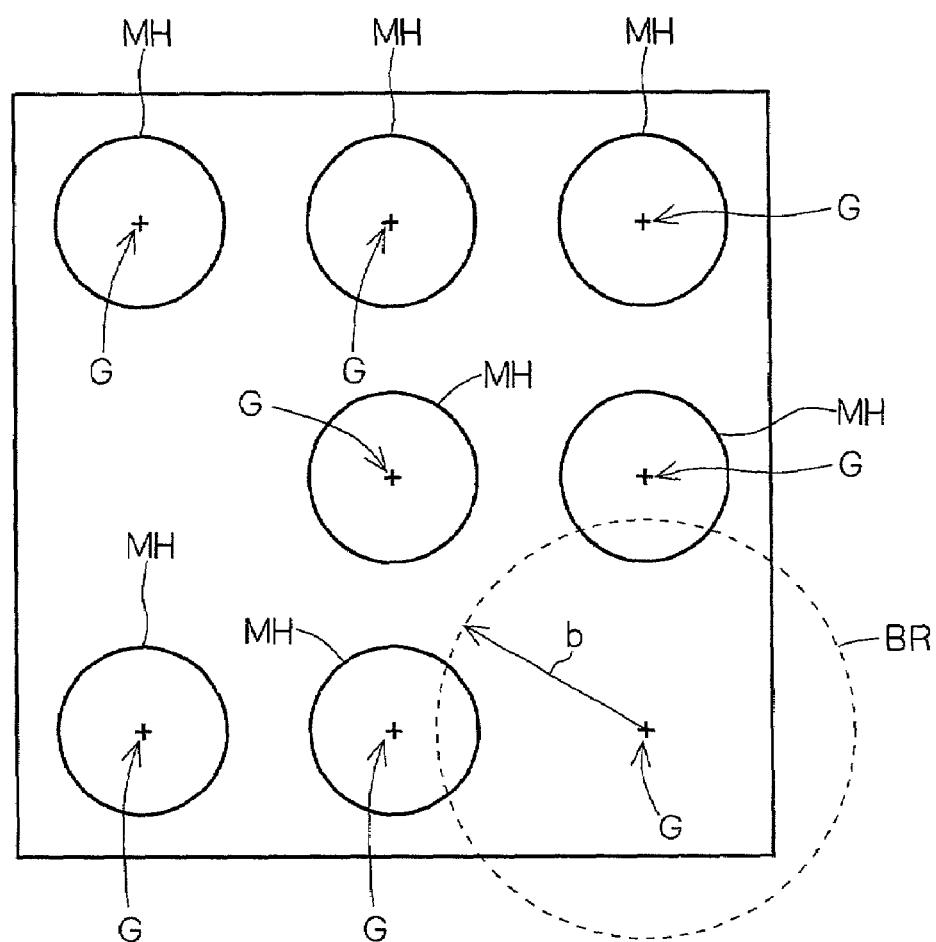
F/G. 17

MH

PH — PZ

MH

PH

G

HOLE INSPECTION APPARATUS AND METHOD

BACKGROUND OF THE INVENTION

1. Field of the Invention

The present invention relates to a hole inspection apparatus inspecting a plurality of holes formed in an inspected object such as a printed board or a substrate for a printed board.

2. Description of the Background Art

A printed board is formed with a large number of through holes (or via holes) passing through the printed board, in order to solder elements onto the printed board or the like. These through holes are generally formed by perforating prescribed positions of the printed board with a drill bit of a drilling machine. Such through holes must be reliably perforated, and hence inspection is performed as to presence/absence of a defect in any through hole.

The defect of the through hole is inspected as follows, for example: First, one surface of a substrate for the printed board is irradiated with illumination light for picking up an image of the rear surface thereof, thereby acquiring image data based on the light transmitted through the through holes. Information (hereinafter also referred to as "hole information") as to the centroidal position of the through holes, the hole diameter, the hole area etc. is calculated from the image data for comparing the results of calculation with design data and detecting whether or not any through hole is defective. Correct inspection results can be obtained by extracting feature quantities in the picked-up image for executing such defect inspection.

While such defect inspection is preferably directed to all through holes, an extremely long time (e.g., two hours for one sheet) is disadvantageously required for calculating hole information as to all through holes over the entire image. Therefore, it is impractical to perform such defect inspection on all through holes, and the so-called "sampling inspection" extracting a partial area including partial through holes and inspecting only this partial area is performed in practice.

Following recent refinement of a wiring pattern formed on the printed board, however, the range of allowable errors for the through holes is reduced. More specifically, the width of land portions formed around the through holes is so reduced that the range of allowable positional errors is also reduced. The diameter of the through holes themselves is reduced, leading to reduction of the diameter of the drill bit itself. When a plurality of substrates are simultaneously perforated with such a thin drill bit, the drill bit is disadvantageously bent on an intermediate position, leading to a high possibility for a defect such as misregistration of the through holes in substrates located on lower portions.

The through holes are defected in a high possibility due to the aforementioned circumstances, and a probability of overlooking such defects is disadvantageously increased in the conventional sampling inspection. Therefore, total inspection for inspecting defects as to all through holes is increasingly required. In order to perform total inspection in practice, the time required for the inspection is desirably reduced by effectively performing the inspection. Such circumstances apply not only to the aforementioned case of providing "holes as through holes" but also to a case of forming general "holes" also including "holes formed in a state indented to intermediate positions along the thickness of an inspected object".

SUMMARY OF THE INVENTION

The present invention is directed to an apparatus for inspecting a plurality of holes formed in an inspected object.

According to the present invention, an apparatus for inspecting a plurality of holes formed in an inspected object comprises image pickup means for picking up an image of the inspected object having the plurality of holes for acquiring object pattern data, storage means for storing master pattern data expressing an ideal state of the inspected object, area division means for dividing the object pattern data into a plurality of object pattern divisional areas having a prescribed size, defect candidate area extraction means for comparing each object pattern divisional area with master pattern data corresponding to each object pattern divisional area thereby determining whether or not each object pattern divisional area is a defect candidate and extracting a defect candidate area from the plurality of object pattern divisional areas, first acquisition means for obtaining first hole information as to holes present in the object pattern divisional area extracted as the defect candidate area from the plurality of object pattern divisional areas, second acquisition means for obtaining second hole information as to holes present in an area of the master pattern data corresponding to the object pattern divisional area extracted as the defect candidate area, and defect determination means for comparing the first hole information and the second hole information with each other for determining whether or not each hole is defective on the basis of a result of comparison.

According to this structure, defects of the holes can be correctly and efficiently inspected.

Preferably, the defect candidate area extraction means comprises i) means for selecting an objective area among the plurality of object pattern divisional areas, ii) means for determining a part of the master pattern area corresponding to the objective area to determine a first reference area, iii) shifting means for shifting the first reference area to respective directions on a two-dimensional plane pixel by pixel within a predetermined pixel number range to obtain a plurality of second reference areas, respectively, iv) comparing means for comparing the objective area with the plurality of second reference areas, and the comparing means comprises means for scanning the objective area and the plurality of second reference areas with a defect inspection window having a size corresponding to a plurality of pixels, and means for counting inconsistent pixels at which the objective area has pixel values different from at least one second reference areas for each scanning position of the defect inspection window, to determine a pattern mismatch when a counted number of the inconsistent pixels are more than a predetermined threshold number, and v) determination means for determining the objective area as the defect candidate area only when the pattern mismatch is found for all of the plurality of second reference areas.

According to this structure, pattern defects can be precisely and efficiently detected while absorbing registration errors.

Preferably, the size of the object pattern divisional areas is so set as to include one hole in each object pattern divisional area at the maximum.

According to this structure, defects of the holes can be more efficiently inspected.

The present invention is also directed to a method of inspecting a plurality of holes formed in an inspected object.

Thus, an object of the present invention is to provide a hole inspection apparatus and a hole inspection method capable of correctly and efficiently inspecting holes.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1 schematically illustrates the structure of a through hole inspection apparatus 1 according to an embodiment of the present invention;

FIGS. 5A and 5B conceptually illustrate a detection method at a step SP30;

FIG. 6 illustrates the circuit structure of a detection circuit 12a;

FIGS. 7A and 7B illustrate exemplary object pattern data and master pattern data specified at a prescribed data input point;

FIG. 9 conceptually illustrates comparison of each comparative detection block $B_{ij}$ at a certain point of time;

FIG. 13 illustrates an exemplary object pattern divisional area $PD_{ij}$ extracted as a defect candidate area;

FIG. 14 illustrates a corresponding area $MD_{ij}$ of a master pattern corresponding to the defect candidate area;

FIG. 15 illustrates the areas $PD_{ij}$ and $MD_{ij}$ in positional correspondence to each other;

FIG. 16 illustrates another exemplary object pattern divisional area $PD_{ij}$ extracted as a defect candidate area;

FIG. 17 illustrates the areas $PD_{ij}$ and $MD_{ij}$ in positional correspondence to each other;

DESCRIPTION OF THE PREFERRED EMBODIMENTS

<A. Structure>

Figure 2:
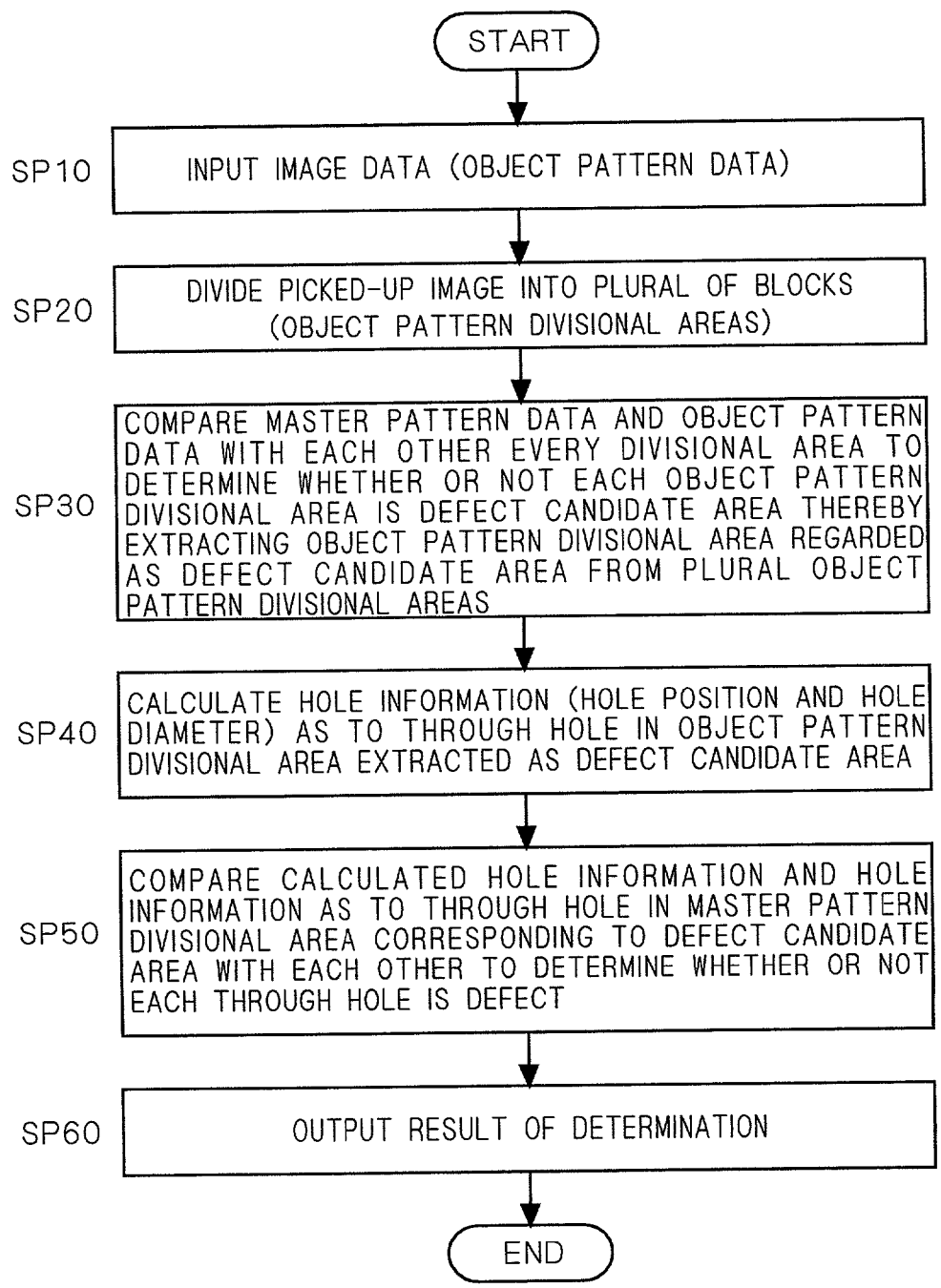
FIG. 2 is a flow chart showing a defect detecting operation.

FIG. 1 schematically illustrates the structure of a through hole inspection apparatus (hole inspection apparatus) 1 according to an embodiment of the present invention. This through hole inspection apparatus 1 inspects presence/absence of defects etc. as to a plurality of through holes H passing through a plate-type member such as a printed board 4 serving as an inspected object. As shown in FIG. 1, this through hole inspection apparatus 1 comprises a movable table 2, a light source 3, a driving/control part 5, an X-directional driving part 6, a Y-directional driving part 7, a CCD line sensor 8, a first image processing part 10, a master pattern data storage part 19 and a second image processing part 20. The first image processing part 10 has an image acquisition part 9, an area division part 11 and a defect candidate area extraction part 12, while the second image processing part 20 has a hole information calculation part 21 and a defect determination part 22. The area division part 11, part of the defect candidate area extraction part 12, the hole information calculation part 21 and the defect determination part 22 are processing parts functionally implemented by executing a prescribed program in a computer system.

The movable table 2, made of a transparent material for transmitting light from the light source 3, can hold the inspected object such as the printed board 4 within a prescribed range of positioning accuracy. The Y-directional driving part 7 including a motor drives the movable table 2 along a direction Y. The driving/control part 5 drives/controls the movable table 2 in the direction Y.

The CCD line sensor 8 is provided above the movable table 2. The CCD line sensor 8 is formed by aligning a plurality of (e.g., 2048) photoreceptors forming pixels on an X-directional line. When the lower surface of the printed board 4 is irradiated with illumination light emitted from the light source 3, this CCD line sensor 8 picks up an image of the opposite surface (the upper surface in FIG. 1) thereby acquiring image data based on the light transmitted through the through holes H.

The X-directional driving part 6 including a motor drives the CCD line sensor 8 in a direction X. The driving/control part 5 drives/controls the CCD line sensor 8 (described later) in the direction X.

In order to read the image of the printed board 4 picked up by the CCD line sensor 8, the Y-directional driving part 7 moves the movable table 2 along the direction Y for zonally scanning the printed board 4 with a scanning width WDa as forward scanning. When the forward scanning is completed, the X-directional driving part 6 moves the CCD line sensor 8 in the direction X by a width slightly smaller than the aforementioned scanning width WDa to overlap inspected areas and then moves the movable table 2 in a direction −Y (minus Y) for performing backward scanning. Thus, the overall area of the printed substrate board 4 is scanned for reading the image.

The image acquisition part 9 converts an analog image signal read by the CCD line sensor 8 to a digital image signal by A/D conversion, and a binarization circuit binarizes the digital image signal to signals "1" and "0" through spatial filtering. Thus, the through hole inspection apparatus 1 can acquire the image of the surface of the printed boar 4 having the plurality of through holes H as a digital image.

The image picked up as to the printed board 4 to be inspected is acquired as object pattern data.

On the other hand, the master pattern data storage part 19 stores master pattern data expressing an ideal state as to the plurality of through holes H of the printed board 4. This master pattern data is created on the basis of design data (CAD data), for example. If a correct printed board 4, i.e., a printed board 4 employable as the inspection standard is present, an image of the printed board 4 employable as the inspection standard picked up with the aforementioned CCD line sensor 8 or the like may alternatively be employed as the master pattern data.

The area division part 11 divides the object pattern data into a plurality of object pattern divisional areas having a prescribed size.

The defect candidate area extraction part 12 determines whether or not each object pattern divisional area has a different portion exceeding a prescribed allowance between the same and an area of the master pattern data corresponding thereto by pattern matching, thereby determining whether or not each object pattern divisional area is a defect candidate (i.e., whether or not the same has a high possibility of including a defect) and extracting an area having a high possibility of including a defect as a "defect candidate area". Thus, the defect candidate area extraction part 12 extracts the defect candidate area from the plurality of object pattern divisional areas.

More specifically, the defect candidate area extraction part 12 sets, as to each of the plurality of object pattern divisional areas, a master pattern divisional area group consisting of a plurality of master pattern divisional areas two-dimensionally misregistered pixel by pixel by a prescribed amount over an extended area formed by extending the periphery of an area of the master pattern data to correspond to each object pattern divisional area by a prescribed number of pixels. And the part 12 compares each object pattern divisional area with the master pattern divisional area group corresponding thereto, and determines whether or not each object pattern divisional area is a defect candidate as described later. The defect candidate area extraction part 12 is preferably formed by a hardware circuit (described later), in order to increase the speed.

The hole information calculation part 21 calculates hole information as to through holes present in the object pattern divisional area extracted from the plurality of object pattern divisional areas as the defect candidate area by the defect candidate area extraction part 12. Further, this hole information calculation part 21 also calculates hole information as to through holes present in the area of the master pattern data corresponding to the object pattern divisional area extracted as the defect candidate area. The hole information calculation part 21 preferably previously obtains the hole information as to the through holes present in the master pattern data in advance of inspection.

The defect determination part 22 compares the hole information as to the through holes present in the object pattern divisional area extracted as the defect candidate area and the hole information as to the through holes present in the area of the master pattern data corresponding to the defect candidate area with each other and determines whether or not each through hole is defective on the basis of the result of comparison.

Thus, presence/absence of defects as to the plurality of holes included in the object pattern data can be obtained as results output from the second image processing part 20. The aforementioned operation is described later in detail.

The through hole inspection apparatus 1 further comprises a visual defect recognition part 30. This visual defect recognition part 30 can expansively display any hole output as defective from the second image processing part 20 so that the through hole displayed on a display part (not shown) of the visual defect recognition part 30 can be compared with the master pattern data by an operator. Therefore, whether or not this through hole is defective can be finally determined through visually recognition.

The through hole inspection apparatus 1 may be systematically formed by integrating a plurality of computers with each other. For example, the first image processing part 10, the second image processing part 20 and the visual defect recognition part 30 may be formed by different computers respectively, or these parts 10, 20 and 30 may be partially or entirely formed as the same computer. When the parts 10, 20 and 30 are formed as different computers, the computers can exchange mutual information through a communication line such as a LAN.

It is assumed that the term "through hole" employed in this specification has a concept including at least both of a through hole in a narrow sense (a through hole having a relatively large diameter employed for receiving an IC terminal or the like) and a via hole (a through hole having a relatively small diameter employed for connecting a signal line or the like), and the following defect detection technique can be applied to both of the through hole and the via hole.

<B. Operation>
<B1. Outline>

The defect inspection in the through hole inspection apparatus 1 is now described. This defect inspection is performed along a flow chart shown in FIG. 2.

More specifically, at a step SP10, the CCD line sensor 8 or the like picks up an image of the printed board 4 to be inspected. As hereinabove described, the image acquisition part 10 acquires image data (hereinafter referred to as "object pattern data") as to the printed board 4 to be inspected on the basis of a signal from the CCD line sensor 8.

At a step SP20, the picked-up image (i.e., the object pattern data) is divided into a plurality of divisional areas (hereinafter referred to as "object pattern divisional areas").

Figure 3B:
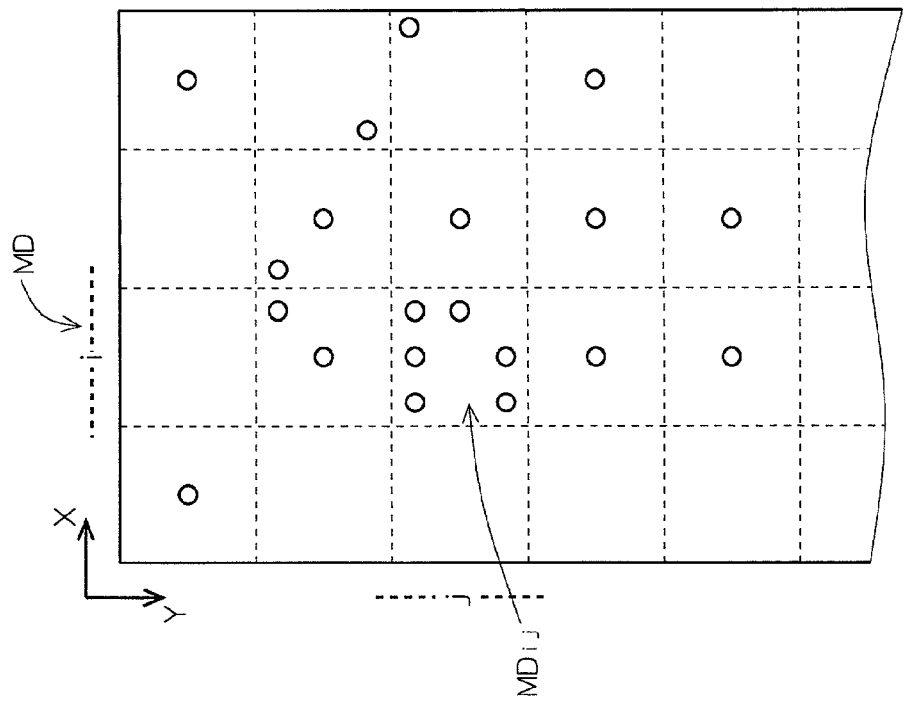
FIGS. 3A and 3B illustrate object pattern data PD and master pattern data MD respectively.
Figure 3A:
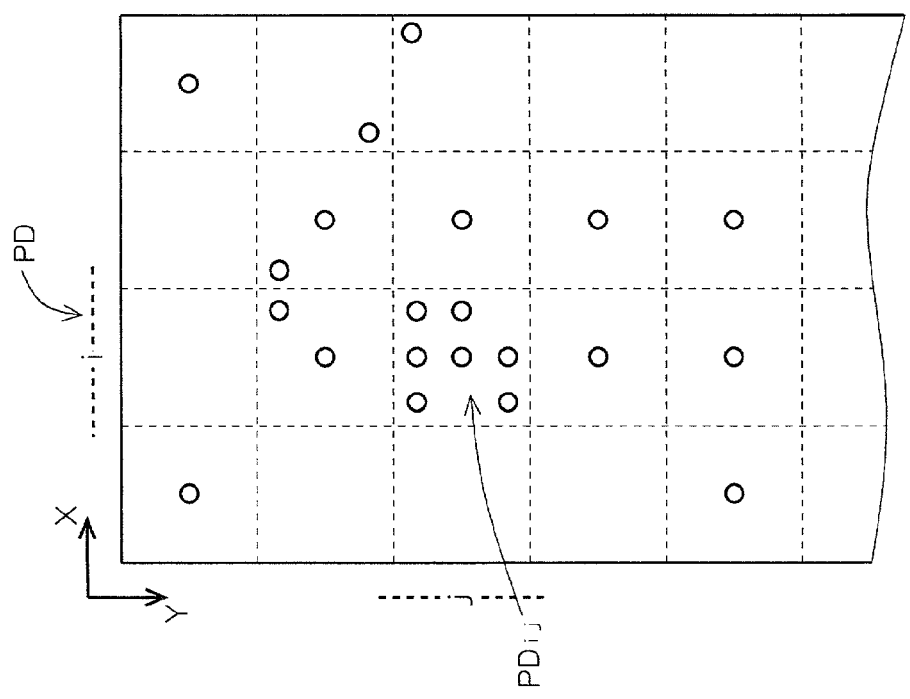

FIGS. 3A and 3B show object pattern data PD and master pattern data MD respectively. FIGS. 3A and 3B display through holes as circles.

As shown in FIG. 3A, the object pattern data PD is divided into divisional areas (i.e., object pattern divisional areas) $PD_{ij}$ each having prescribed numbers of pixels in the directions X and Y respectively. Assuming that the object pattern data PD has 2048 pixels in total in the direction X, for example, each divisional area $PD_{ij}$ obtained by dividing the object pattern data PD into four along the direction X has 512 (=2048/4) pixels in the direction X. When the object pattern data PD is divided to have the same number of pixels also in the direction Y, each divisional area $PD_{ij}$ is defined as a square divisional area having 512 by 512 pixels.

FIG. 3B shows corresponding areas $MD_{ij}$ of the master pattern data MD positionally corresponding to the respective object pattern divisional areas $PD_{ij}$. Each corresponding area $MD_{ij}$ corresponds to each object pattern divisional area $PD_{ij}$ having the same number of pixels. In other words, each object pattern divisional area $PD_{ij}$ matches with each corresponding area $MD_{ij}$ when the object pattern data PD and the master pattern data MD are identical to each other. While FIGS. 3A and 3B illustrate square areas $PD_{ij}$ and $MD_{ij}$, the present invention is not restricted to this but transverse or vertical rectangular areas may alternatively be employed.

As described later, a master pattern divisional area group consisting of a plurality of master pattern divisional areas two-dimensionally misregistered pixel by pixel by a prescribed quantity over an extended area formed by extending the periphery of the corresponding area $MD_{ij}$ by a prescribed number of pixels is set as to each object pattern divisional area $PD_{ij}$.

At a next step SP30, the object pattern data PD and the master pattern data MD are compared with each other every corresponding divisional area. More specifically, each object pattern divisional area $PD_{ij}$ is compared with a plurality of master pattern divisional areas included in the master pattern divisional area group corresponding thereto, respectively. Whether or not each object pattern divisional area $PD_{ij}$ is a defect candidate area is determined in response to the results of comparison. The object pattern divisional area $PD_{ij}$ regarded as the defect candidate area is decided from the plurality of object pattern divisional areas $PD_{ij}$. This operation is described later in detail.

At a step SP40, hole information (the centroidal position, the area and the diameter) as to the through holes of the object pattern divisional area $PD_{ij}$ extracted as the defect candidate area is calculated. This operation is also described later in detail.

Thereafter the hole information calculated at the step SP40 is compared with hole information as to through holes in the area $MD_{ij}$ of the master pattern corresponding to the defect candidate area, for determining whether or not each through hole is defective at a step SP50.

The result of this determination as to whether or not each through hole is defective is output to a display (not shown) of the through hole inspection apparatus 1 at a step SP60. Thereafter the operator can finally confirm whether or not the through holes in the actual printed board 4 to be inspected are defects by observing the image of the through holes in the defect candidate area expansively displayed on the visual defect recognition part 30 with reference to the result of determination.

<B2. Detailed Operation of First Stage (Step SP30)>

The operation at the step SP30 (hereinafter also referred to as "first-stage operation") is now described in detail.

Also when the inspected object has a registration error resulting from misregistration or distortion, a pattern defect can be accurately detected while absorbing this registration error and the pattern defect detection can be quickly performed by carrying out the first-stage operation.

The first-stage operation is so executed as to extract the object pattern divisional area $PD_{ij}$ regarded as the defect candidate area from the plurality of object pattern divisional areas $PD_{ij}$. Plainly stated, the range of areas subjected to the next steps SP40 and SP50 is limited due to the first-stage operation (the operation at the step SP30).

<Principle>

The principle of the operation at the step SP30 is now described.

(1: Discussion as to Basic Pattern Matching)

Figure 4A:
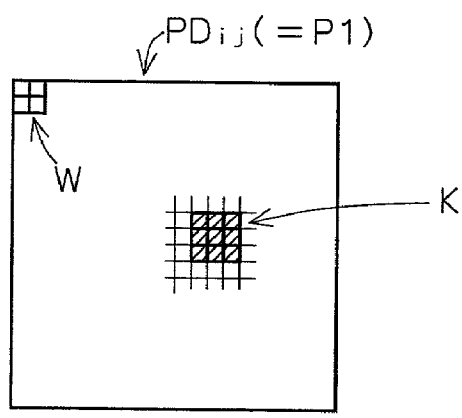
FIGS. 4A and 4B illustrate a basic operation of pattern matching.
Figure 4B:
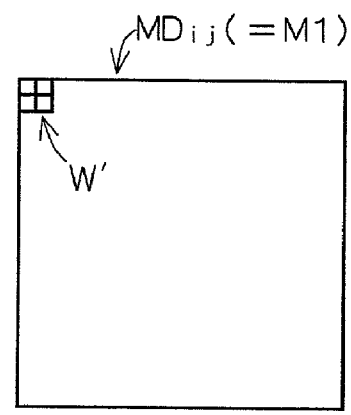

Assuming that the inspected object is correctly located on a prescribed position of an inspection mechanism with no quantization error, a case of performing pattern defect detection with the following basic pattern matching is discussed. It is assumed that an object pattern divisional area P1 is scanned with an inspection window W (assumed to have 2 by 2 pixels here) consisting of a size of a plurality of pixels corresponding to a defect size as shown in FIG. 4A, while a corresponding area M1 of the master pattern is similarly scanned with an inspection window W' of the same pixel size in positional correspondence to the inspection window W as shown in FIG. 4B, for performing pattern defect inspection by basic pattern matching of comparing binarized signals of a plurality of images included in the inspection windows W and W' with each other. If the inspected object has no pattern defect, there is no portion where all pixels in the inspection windows W and W' mismatch with each other.

If the inspected object has a pattern defect, on the other hand, it follows that there is a portion where all binarized signals of corresponding pixels in the inspection windows W and W' mismatch with each other (hereinafter referred to as "inspection window mismatch"). This is because the size of the inspection window W corresponds to the defect size.

Thus, if the inspected object has no misregistration, the aforementioned comparison is performed by scanning all areas (or prescribed areas) in the patterns with the inspection windows W and W' so that presence of a pattern defect can be determined when the inspection windows W and W' mismatch with each other at least in a portion and absence of the pattern defect can be determined when the inspection windows W and W' match with each other in all portions.

While the pattern defect can be sufficiently detected by the aforementioned pattern matching when the inspected object has no misregistration, the inspected object has a misregistration error resulting from misregistration (including not only vertical and horizontal shifting but also inclined shifting) or distortion in practice as described above, and hence it follows that a detection error of the pattern defect is caused in the aforementioned method. The reason for this is now described.

It is assumed that an inspected object having no pattern defect is set and image-input in the inspection mechanism in a misregistered state (e.g., in a state having a registration error), e.g., in a state misregistered by −2 pixels in the direction X (two pixels leftward) and −2 pixels in the direction Y (two pixels upward), to result in an object pattern $P_0'$ (on a position $P_0$ in FIG. 5A as described later). If this object pattern $P_0'$ is compared with a master pattern M for detecting a pattern defect by the aforementioned basic pattern matching, the inspection windows W and W' mismatch with each other on a considerably large number of scanning positions, leading to determination of pattern defects although there is no pattern defect.

(2: Pattern Matching at Step SP30)

At the step SP30, therefore, defect detection is performed by a method capable of correctly detecting a pattern defect by absorbing a misregistration error if the inspected object has misregistration, in consideration of the aforementioned problem.

FIGS. 5A and 5B conceptually show the detection method at the step SP30. A plurality of master pattern areas (master pattern divisional areas), two-dimensionally misregistered pixel by pixel in every direction by a prescribed quantity over an area prepared by extending the periphery of a master pattern area $M_0$ positionally corresponding to a reference position $P_0$ (the position of an object pattern P in a case where the inspected object is correctly set on a prescribed position) of the object pattern (more specifically, an object pattern divisional area) P, are set for comparing a plurality of master patterns $M_{11}$ to $M_{77}$ with the object pattern $P_0'$ respectively and performing pattern defect detection. In this case, the extended master pattern area is set in a range capable of absorbing a misregistration error (registration error) resulting from misregistration or distortion of the inspected object. FIGS. 5A and 5B illustrate the case where the extended master pattern area is set vertically and horizontally misregistered by three pixels about the area $M_0$.

When such a plurality of master patterns $M_{11}$ to $M_{77}$ are set, it follows that a master pattern positionally corresponding to the object pattern P is present as one of the master patterns $M_{11}$ to $M_{77}$ also when the inspected object is misregistered. Referring to FIG. 5A, it is assumed that the object pattern P is placed with misregistration by two pixels upward and two pixels leftward with respect to the reference position $P_0$, and hence the master pattern exactly registered with the object pattern $P_0'$ present on the reference position $P_0$ in this case is not the master pattern $M_{44}$ to originally match on this position but the master pattern $M_{66}$ present on the position misregistered from the area $M_0$ ($M_{44}$) by two pixels downward and two pixels rightward.

After such a master pattern area group (i.e., a master pattern divisional area group) is set, the object pattern P is compared with each of the master patterns $M_{11}$ to $M_{77}$ by the aforementioned basic pattern matching. The defect inspection windows W and W' each having the size corresponding to a plurality of pixels are respectively set in the misregistered object pattern $P_0'$ and each of the master patterns $M_{11}$ to $M_{77}$, for scanning the overall patterns with the inspection windows W and W' positionally corresponding to each other and determining pattern mismatch when the inspection windows W and W' mismatch with each other at least in one portion while otherwise determining pattern match. Thus, in the comparison between the object pattern $P_0'$ and the master pattern ($M_{66}$ in FIGS. 5A and 5B) positionally corresponding to each other, pattern match is determined (found) if the inspected object has no pattern defect while pattern mismatch is determined (found) if there is a pattern defect (if there is no quantization error and the inspected object has no pattern defect, pattern match is determined also as to the master patterns $M_{55}$, $M_{56}$, $M_{57}$, $M_{65}$, $M_{67}$, $M_{75}$, $M_{76}$ and $M_{77}$ in addition to the master pattern $M_{66}$ in FIGS. 5A and 5B). In comparison between the object pattern $P_0'$ and the remaining master patterns ($M_{11}$ to $M_{77}$ excluding the master patterns $M_{55}$, $M_{56}$, $M_{57}$, $M_{65}$, $M_{66}$, $M_{67}$, $M_{75}$, $M_{76}$ and $M_{77}$ in FIGS. 5A and 5B), the patterns to be compared with each other are positionally misregistered to cause mismatch of the inspection windows W and W', and hence determination is made on pattern mismatch.

Pattern defect detection is performed by determining presence of a pattern defect when determination of pattern mismatch is made on all master patterns $M_{11}$ to $M_{77}$ included in the master pattern area group while determining absence of a pattern defect when determination of pattern match is made on at least one master pattern.

According to this method setting the plurality of master patterns $M_{11}$ to $M_{77}$ two-dimensionally misregistered pixel by pixel within a predetermined pixel number range as those to be compared with the object pattern $P_0'$, high-accuracy pattern defect detection can be performed by absorbing a registration error also when the inspected object has misregistration or the registration error. Also when the object pattern P or any of the master patterns $M_{11}$ to $M_{77}$ includes a quantization error in a case where an end of the pattern is present within an area of one pixel or a quantization error resulting from inclined arrangement of the pattern, corresponding binarized signals of pixels included in the inspection windows W and W' do not entirely mismatch with each other in the comparison between the object pattern P and at least one master pattern, and hence false defect detection resulting from the quantization error can also be prevented.

While the pattern defect detection method at the step SP30 has been schematically described, a large-scale circuit is required if the aforementioned method is executed as such. In practice, therefore, the following simplified circuit is preferably employed.

<Specific Structure and Specific Operation>

Figure 6:
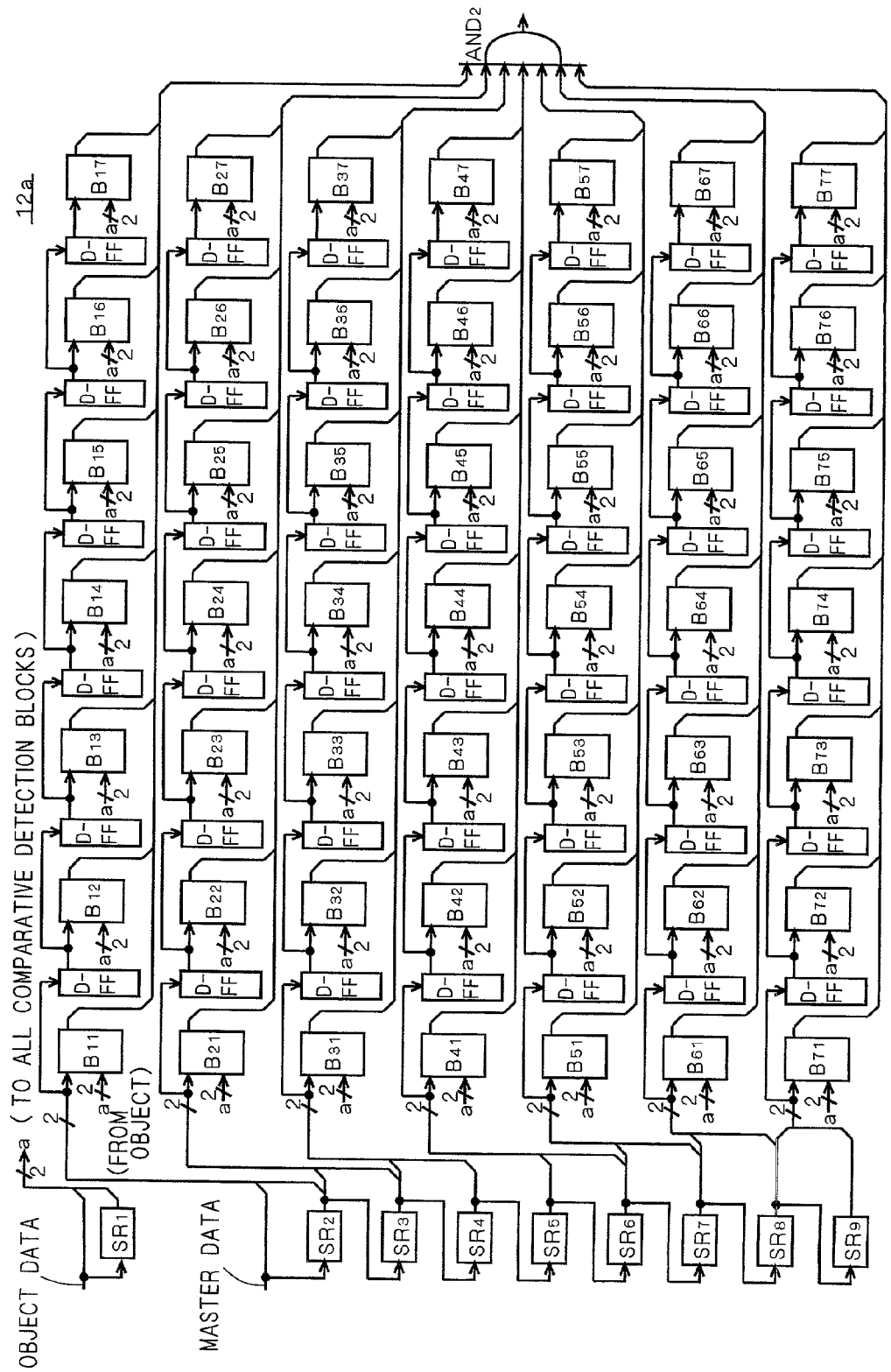

FIG. 6 illustrates the circuit structure of a detection circuit 12a provided in the defect candidate area extraction part 12. Image data (object pattern data) of the object pattern $P_0'$ obtained by scanning the inspected object is binarized and time-serially input in this detection circuit 12a. At the same time, binarized data (master pattern data) of the master pattern M called from a memory is time-serially input in synchronization with the input of the object pattern data (hereinafter also simply referred to object data). While each of the object pattern divisional areas $PD_{ij}$ and the corresponding areas $MD_{ij}$ of the master pattern M has the size of 512 by 512 pixels in the above, it is assumed in the following description that each of the object pattern divisional areas $PD_{ij}$ and the corresponding areas $MD_{ij}$ of the master pattern M has a size of 32 by 32 pixels, in order to simplify the illustration.

The object data input in the aforementioned manner is input in comparative detection blocks $B_{11}$ to $B_{77}$ in a pair with the object data delayed by one line (32 pixels) by a shift register $SR_1$. 49 such comparative detection blocks $B_{11}$ to $B_{77}$ are provided in correspondence to the master patterns $M_{11}$ to $M_{77}$ shown in FIG. 5B.

On the other hand, the master pattern data (hereinafter also simply referred to as master data) input in a defect inspection part is separated by shift registers $SR_2$ to $SR_9$ to be delayed line by line, so that pairs of data adjacent to each other along the direction of separation are input in horizontal stages of the comparative detection blocks $B_{11}$ to $B_{77}$ with misregistration of one line and delayed by D-type flip-flops D-FF inserted every vertical stage by one pixel every vertical stage. Thus, all pairs of master data supplied to the comparative detection blocks $B_{ij}$ (i=7 and j=7) respectively are two-dimensionally misregistered pixel by pixel. The timing for inputting the object data and the master data in the detection circuit 12a is set as follows: When the inspected object is correctly located on a prescribed position of the inspection mechanism and data of an area E1 of the object pattern P shown in FIG. 7A is input in the comparative detection blocks $B_{11}$ to $B_{77}$ in common, data of areas $E_{11}$ to $E_{77}$ two-dimensionally misregistered pixel by pixel shown in FIG. 7B are simultaneously separately input in the corresponding comparative detection blocks $B_{11}$ to $B_{77}$ respectively. Thus, also when the inspected object is misregistered, it follows that the area E1 of the misregistered object pattern $P_0'$ positionally corresponds to one of the areas $E_{11}$ to $E_{77}$ of the master pattern M, and this also applies to the remaining areas of the object pattern $P_0'$.

Figure 8:
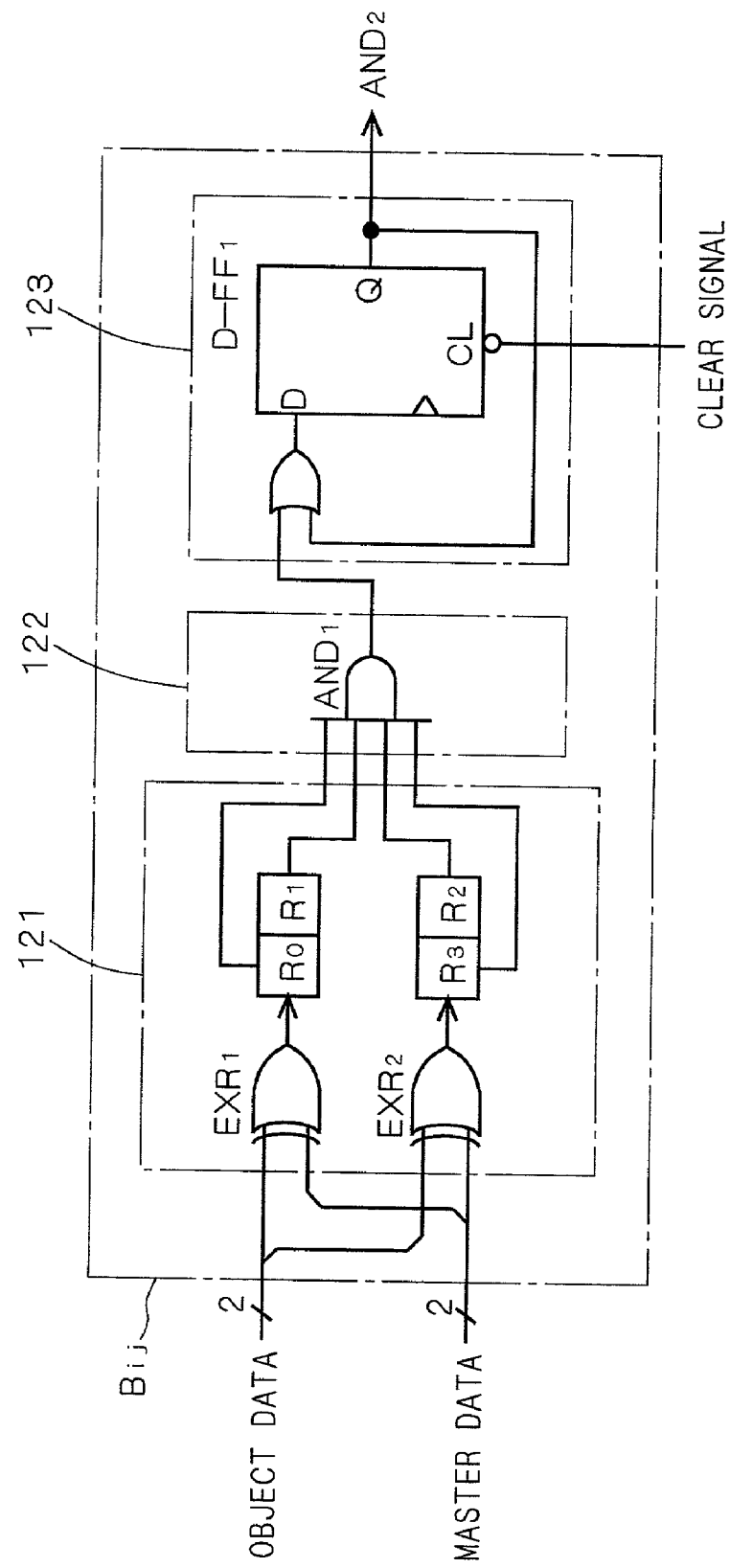
FIG. 8 is a specific circuit diagram of a comparative detection block.

FIG. 8 is a specific circuit diagram of each of the aforementioned comparative detection blocks $B_{ij}$ (i=7 and j=7). The comparative detection blocks $B_{ij}$ are identical in structure to each other, and hence FIG. 8 shows the circuit of only one comparative detection block $B_{ij}$.

This comparative detection block $B_{ij}$ is formed by a comparator 121, a determination circuit 122 and a holding circuit 123. The comparator 121 compares the object data and the master data input in pairs respectively with each other every corresponding pixel by exclusive OR gates $EXR_1$ and $EXR_2$ for outputting "1" if binarized signals of the corresponding pixels mismatch with each other while outputting "0" if the same match with each other, so that shift registers $R_0$ and $R_3$ latch the results respectively. Also when next object data and master data are input, the comparator 121 compares the same with each other by the exclusive OR gates $EXR_1$ and $EXR_2$, so that the shift registers $R_0$ and $R_3$ latch the results respectively. At this time, the data having been latched in the shift registers $R_0$ and $R_3$ are shifted to adjacent shift registers $R_1$ and $R_2$ respectively. Every time the object data and the master data are input, the comparator 121 compares the same with each other by the exclusive OR gates $EXR_1$ and $EXR_2$ and sequentially shifts the results of comparison through the shift registers $R_0$ to $R_3$. The results latched in the shift registers $R_0$ to $R_3$ correspond to the results of comparison every corresponding pixels in the inspection windows W and W' shown in FIGS. 5A and 5B.

The determination circuit 122 inputs the data latched in the shift registers $R_0$ to $R_3$ in an AND gate $AND_1$ every time the results are shifted through the shift registers $R_0$ to $R_3$, for outputting data "1" to the holding circuit 123 when all of the data latched in the shift registers $R_0$ to $R_3$ mismatch with each other (i.e., when there is a mismatch portion corresponding to a defect size) while outputting data "0" to the holding circuit 123 when at least one of data match with each other.

The holding circuit 123 ANDs a Q output signal from a D-type flip-flop D-FF$_1$ and an output signal from the aforementioned AND gate AND$_1$, and holds the result in the D-type flip-flop D-FF$_1$. Thus, it follows that the D-type flip-flop D-FF$_1$ holds the data "0" until a mismatch portion corresponding to the defect size appears while holding the data "1" if at least one mismatch portion corresponding to the defect size appears as the scanning with the inspection windows W and W' progresses.

As hereinabove described, the object data is input in the aforementioned comparative detection blocks B in common while the master data is two-dimensionally misregistered pixel by pixel and input in the respective comparative detection blocks B$_{ij}$. When the area of the object pattern P$_0$' is completely scanned, therefore, it follows that the object pattern P$_0$' shown in FIGS. 5A and 5B is consequently compared with each of master patterns M$_{11}$ to M$_{77}$ in the comparative detection blocks B$_{11}$ to B$_{77}$, and the holding circuits 123 of the respective comparative detection blocks B$_{11}$ to B$_{77}$ hold the respective results of comparison.

Figure 9:
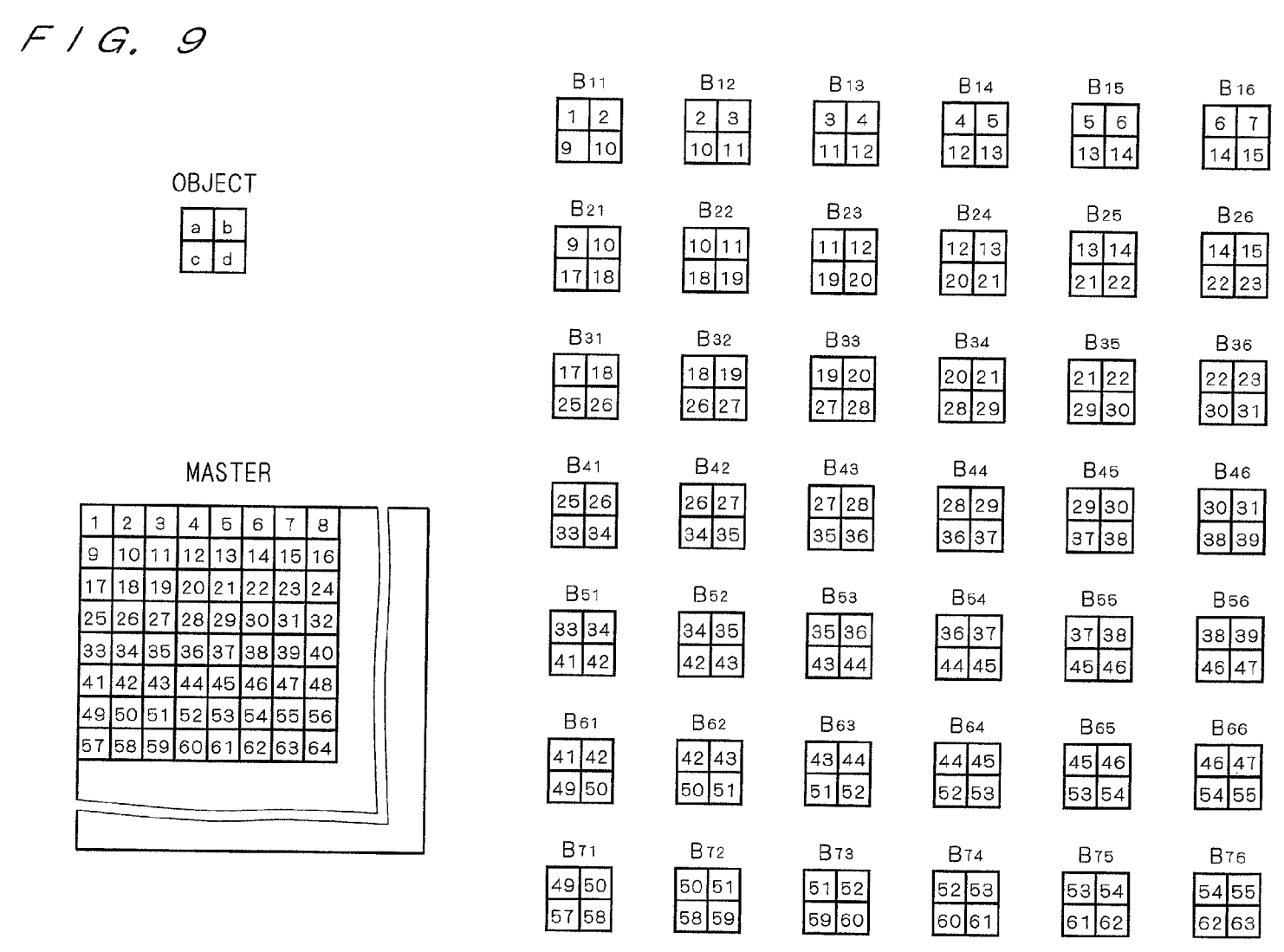

In order to further simplify understanding, comparison in each comparative detection block B$_{ij}$ is imaginably described. FIG. 9 conceptually illustrates comparison in each comparative detection block B$_{ij}$ at a certain point of time. Referring to FIG. 9, 49 blocks located on the right side express the shift registers R$_0$ to R$_3$ of the corresponding comparative detection block B$_{ij}$, and numerals in the blocks express those of corresponding four-pixel areas in the master pattern to be compared with an object area consisting of four pixels a to d. The numerals in these blocks are shifted leftward pixel by pixel every time object data is input. When data in the 49 blocks located on the right side in FIG. 9 for expressing the shift registers R$_0$ to R$_3$ of the corresponding comparative detection block B$_{ij}$ are shifted rightward, it means that the inspection windows W and W' shown in FIGS. 5A and 5B scan the areas rightward. When the overall pattern areas are completely scanned, therefore, it follows that each comparative detection block B$_{ij}$ has compared the object pattern P$_0$' shown in FIGS. 5A and 5B with the master patterns M$_{11}$ to M$_{77}$.

All data held in the holding circuits 123 of the comparative detection blocks B$_{ij}$ are transferred to an AND gate AND$_2$ as shown in FIG. 6, to be subjected to ANDing. As hereinabove described, when the area of the object pattern P$_0$' is completely scanned, the data held in the holding circuit 123 of each comparative detection block B$_{ij}$ becomes "1" if at least one mismatch portion is included in the pattern while becoming "0" if there is no mismatch portion. Therefore, all comparative detection blocks B$_{ij}$ output "1" and an output from the AND circuit AND$_2$ becomes "1" if the inspected object has at least one pattern defect, while at least one positionally corresponding comparative detection block (B$_{66}$ in FIGS. 5A and 5B) outputs "0" and the output of the AND circuit AND$_2$ becomes "0" if the inspected object has no pattern defect. Then, the pattern defect is detected on the basis of the signal output from the AND circuit AND$_2$ after completion of pattern scanning. Thus, when single pattern scanning is completed for detecting presence/absence of the pattern detect and transmitting the result to a next stage (not shown), the contents of the holding circuit 23 are set to "0" with a clear signal.

Whether or not a "pattern defect" is present in any object pattern divisional area can be detected by performing the first-stage operation, as hereinabove described. A divisional area having a pattern defect is extracted as a "defect candidate area". In other words, the divisional area having a pattern defect can be specified and extracted from the plurality of object pattern divisional areas as the "defect candidate area". Thus, the pattern divisional areas having a high possibility of including defects related to the through holes can be chosen. Whether or not the defect of the through holes is present in the divisional area having the pattern defect in practice is inspected by operations following the subsequent step SP40.

The wording "pattern defect" means presence of a different point as a pattern, and the pattern defect does not immediately mean a "defect related to through holes".

The reason of the above is that even if any object pattern divisional area is determined as defective at the aforementioned step SP30, the shift amount of through holes present therein may be within the range of allowable errors. If presence of a defect of through holes is determined only following detection of the pattern defect, there is a possibility of falsely determining a non-defective through hole as defective and performing excess defect detection (false detection). In order to prevent excess defect detection and improve inspection accuracy, the operations following the subsequent step SP40 are further performed for inspecting whether or not each through hole in each object pattern divisional area is defect in further detail.

Now, it is also possible to slightly improve the accuracy of defect detection related to the through holes by adjusting the size of the set range and the shape of the plurality of master pattern areas set for the reference position P$_0$ of the object pattern P and/or adjusting the size, shape etc. of the inspection windows W and W' in the aforementioned processing at the step SP30.

For example, while the master pattern area has a square shape in the aforementioned embodiment, the present invention is not restricted to this but the master pattern area may alternatively have a circular shape. If the master pattern area has a circular shape, excess defect detection resulting from anisotropy can be prevented. When the master pattern area has a square shape as described above, the distances between the center and the ends of the area are different in the direction X (or the direction Y) and an oblique direction of 45° (more specifically, the ratio therebetween is 1:(square root of 2)), and hence shift amounts allowed in the first-stage operation vary with the directions. When the master pattern area has a circular shape, however, the distances between the center and the ends of the area are identical to each other in all directions and hence the shift amounts allowed in the first-stage operation are equalized to each other. Defect detection accuracy related to the through holes can be improved by equalizing the allowable shift amounts in the respective directions with each other.

Figure 21A:
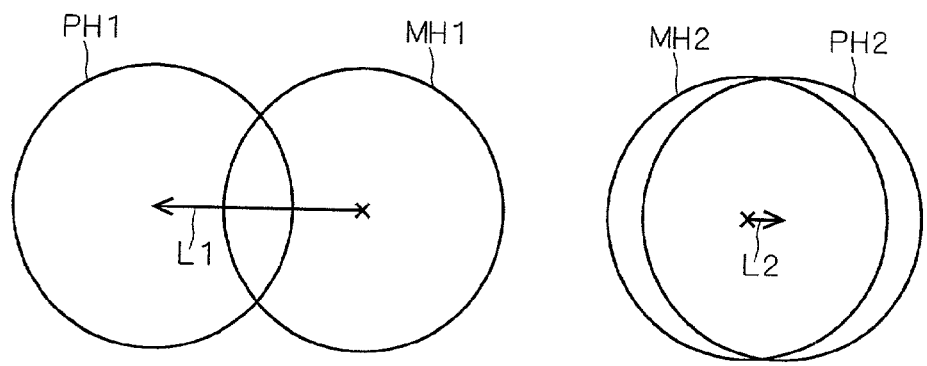
FIGS. 21A to 21C illustrate incorrect defect detection resulting from only a first-stage operation.
Figure 21B:
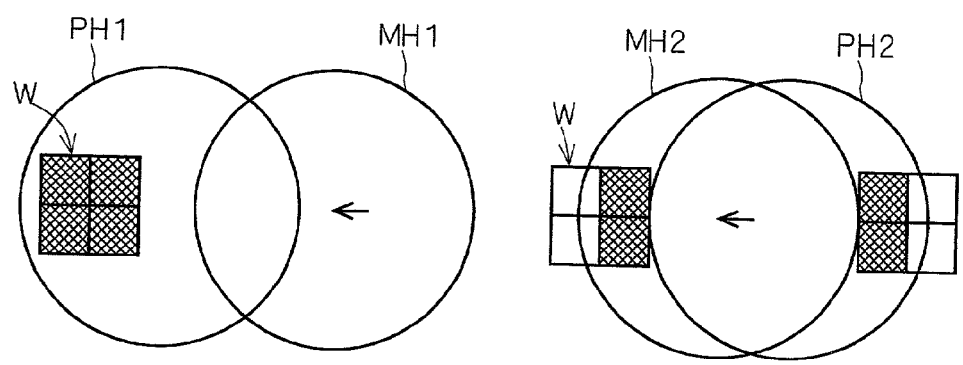
Figure 21C:
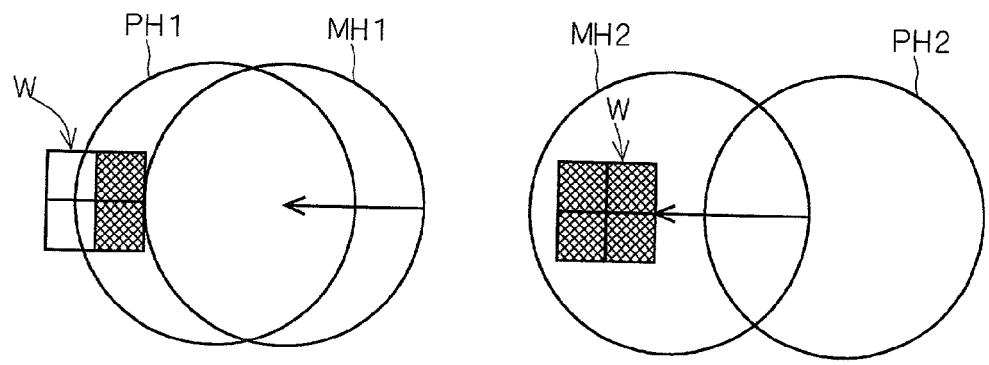

However, it may be difficult to perform correct defect detection only by the first-stage operation. FIGS. 21A to 21C illustrate such difficulty in defect detection. It is assumed that a single divisional area has two through holes. Two through holes PH1 and PH2 in object data "shift" from regular positions respectively with different shift amounts. More specifically, it is assumed that the left through hole PH1 shifts leftward from the regular position by a distance L1 and the right through hole PH2 shifts rightward from the regular position by a distance L2. It is also assumed that the shift amounts L1 and L2 are in an allowable range, and the size of an inspection window W is so set that the distance L1 is the maximum allowable value for the shift amounts of the through holes PH1 and PH2.

In this case, a master pattern is gradually shifted leftward to minimize the difference between the patterns.

Referring to FIG. 21B, the master pattern is slightly shifted leftward, while the through hole PH1 corresponding to a through hole MH1 of the master pattern is still determined as having pattern mismatch. This is because the inspection window W has all pixels within different areas of the left through hole PH1 and the left through hole MH1 of the master pattern. It is assumed that the current shift amount of the right through hole PH2 defines the maximum allowance limit.

When the master pattern is further shifted leftward and the through hole MH2 is shifted leftward beyond the state shown in FIG. 21B, the right through hole PH2 is determined as having pattern mismatch this time. This is because the inspection window W has all pixels in the different areas of the right through hole PH2 and the right through hole MH2 of the master pattern.

When the through hole MH2 is further shifted leftward to reach the state shown in FIG. 21C, the left through hole PH1 is finally determined as presenting pattern match.

In an intermediate state between those shown in FIGS. 21B and 21C, both of the through holes PH1 and PH2 are determined as having pattern mismatch.

Thus, it is understood that there is no state where both of the through holes PH1 and PH2 are determined as presenting pattern match. This means that the through holes PH1 and PH2 having shift amounts not more than the maximum allowable value L1 are determined as having pattern mismatch. When this determination on pattern mismatch is employed for determining defects of the through holes as such, it follows that excess detection is caused in defect detection of the through holes.

As hereinabove described, it may be difficult to perform correct defect detection as to the through holes only through the first-stage operation.

This problem can be solved and defect detection of the through holes can be more correctly performed by further carrying out the operations (extraction and comparison of feature quantities of respective through holes) following the subsequent step SP40.

<B3. Second Stage Operation>

The operations at the steps SP40 and SP50 are now described in detail. The operations at these steps SP40 and SP50 are referred to as a "second-stage operation".

In the second-stage operation, feature extraction is performed as to all through holes included in an object pattern divisional area extracted as a defect candidate area while determining whether or not each through hole H is defective on the basis of the quantity of the extracted feature (hole information).

<Step SP40 (Calculation of Position, Area and Diameter>

More specifically, all through holes PH included in the object pattern divisional area extracted as the defect candidate area at the step SP30 are detected at the step SP40, for calculating "hole information" such as the central position, the area and the diameter as to each through hole PH. The hole information calculation part 21 performs this operation.

Figure 10:
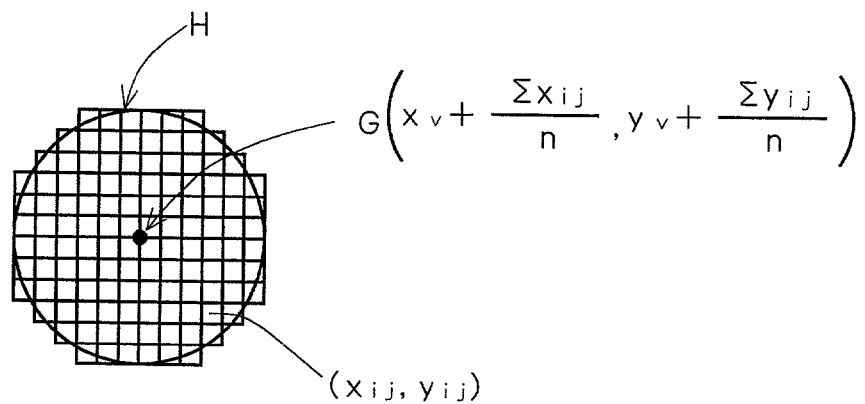
FIG. 10 illustrates calculation of the centroidal position and the diameter of a through hole.

First, the central position of each through hole H is calculated. As shown in FIG. 10, the central position of the through hole H can be calculated as the centroidal position G of pixels forming the through hole H in an image. Assuming that the relative position of each pixel with respect to a reference position $(x_v, y_v)$ is expressed as $(x_{ij}, y_{ij})$, the centroidal position G of the through hole H can be expressed as $(x_v + \Sigma x_{ij}/n, y_v + \Sigma y_{ij}/n)$, where n represents the number of the pixels forming the through hole H. It is assumed that $\Sigma(*)$ indicates the total sum related to all pixels forming the through hole H. If the through hole H has a normal shape, the centroidal position G matches with the center of the circle.

Then, the area R and the diameter D of each through hole H are obtained. The area R is obtained by multiplying the number n of the pixels forming the through hole H by the unit area r of each pixel, i.e., $R = n \times r$. The diameter D of the through hole H is calculated as $D = SQRT(4 \times n \times r/\pi)$ through relation $R = \pi \times (D/2)^2$, where $SQRT(*)$ is assumed to express the square root of the parenthesized value.

Hole information as to through holes included in a master pattern area corresponding to the object pattern divisional area extracted as the defect candidate area is previously obtained in advance of this inspection (in advance of the step SP10). More specifically, hole information as to the position, the area and the diameter of each through hole H is previously obtained on the basis of CAD data or the like and stored in the master pattern storage part 19. The information as to the through holes in the area of the master pattern corresponding to the defect candidate area is called and utilized in comparative determination at the subsequent step SP50.

While the hole information as to the through holes included in the corresponding area of the master pattern is previously obtained in the above, the hole information as to the through holes included in the corresponding area of the master pattern may alternatively be obtained when obtaining the hole information as to the through holes included in the object pattern divisional area.

<Step SP50 (Detection of Defective State>

At the subsequent step SP50 (FIG. 2), study is made as to whether or not each through hole H is defective with the information as to the centroidal position, the diameter etc. of the through hole H obtained in the aforementioned manner.

Defects of the through hole H include:

(1) a "misregistration defect" where the through hole H is not formed on a prescribed position, (2) a "hole diameter defect" where the diameter of the through hole H is excessively large or small, (3) an "unperforated defect" where no through hole H is formed, (4) an "excess hole defect" where the through hole H is excessively formed, (5) a "chip clogging defect" where the through hole H is clogged with a chip, and (6) a "hole deformation defect" where the through hole H is deformed.

Figure 11:
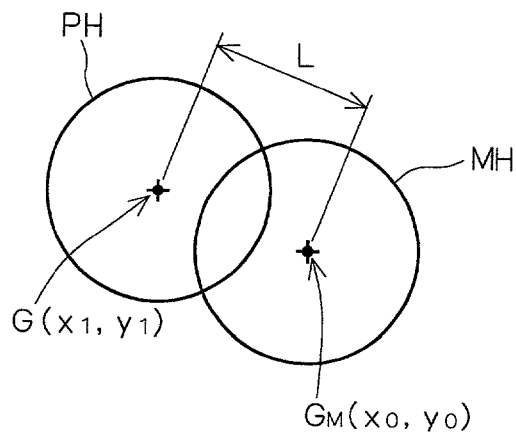
FIG. 11 is a diagram for illustrating detection of a "misregistration defect"

The processing of detecting the "misregistration defect" is described with reference to FIG. 11. FIG. 11 shows a through hole MH present on a normal position in the master data and a through hole PH on the object data imaged in a misregistered state in positional superposition.

Assuming that the coordinate position of the centroidal position G of the through hole PH is obtained as $(x_1, y_1)$ and that of the centroidal position $G_M$ of the through hole MH is obtained as $(x_0, y_0)$ in the processing at the step SP40, the shift amount L therebetween is obtained as follows:

$$L = SQRT((x_1-x_0)^2 + (y_1-y_0)^2)$$

Whether or not each through hole is defective is determined by comparing the shift amount L with a prescribed allowance $L_0$. More specifically, the through hole is determined as defective when the shift amount L is greater than the allowance $L_0$ ($L > L_0$), while the through hole is determined as not defective when the shift amount L is no more than the allowance $L_0$ ($L \leq L_0$).

Figure 12:
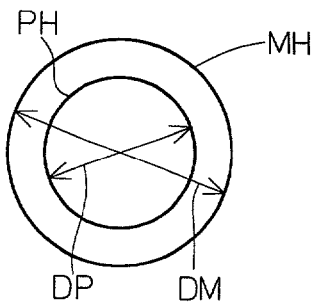
FIG. 12 is an explanatory diagram for illustrating detection of a "hole diameter defect"

Detection of the "hole diameter defect" is now described with reference to FIG. 12. The hole diameter defect is determined by comparing the difference A ($=DP-DM$)

between the diameters DP and DM of the through holes PH and MH with a prescribed allowance $A_0$. More specifically, the through hole is determined as defective when the difference A is less than a negative allowance AL or greater than a positive allowance AH (A<AL or A>AH), while the through hole is determined as not defective when the difference A is no less than the allowance AL and no more than the allowance AH (AL≦A≦AH). It is understood that the diameter of the through hole is excessively smaller than a theoretical value if the difference A is less than the negative allowance AL (A<AL), while the diameter of the through hole is excessively greater than the theoretical value if the difference A is greater than the positive allowance AH (A>AH).

While defect determination of each through hole is performed by comparing the difference (or the shift amount) A between the diameters of the through holes PH and MH, the diameter DP of the through hole PH is calculated through the area R and the relation $R=\pi \times (D/2)^2$ and hence the aforementioned detect determination of each through hole is equivalent to comparison of the difference (or the shift amount) between the areas of the through holes PH and MH and a prescribe allowance.

Detection of the "unperforated defect" is now described with reference to FIGS. 13 to 15. FIG. 13 illustrates an exemplary object pattern divisional area $PD_{ij}$ extracted as the defect candidate area, and FIG. 14 illustrates an exemplary area $MD_{ij}$ of the master pattern corresponding to the object pattern divisional area $PD_{ij}$. FIG. 15 illustrates the object pattern divisional area $PD_{ij}$ and the corresponding area $MD_{ij}$ in positional correspondence to each other. In FIG. 15, solid circles express through holes PH in the object pattern divisional area $PD_{ij}$, while crosses express centroidal positions $G_M$ of through holes MH in the corresponding area $MD_{ij}$ of the master pattern. Referring to FIG. 15, centroidal positions G of the through holes PH and circles showing the contours of the through holes MH are omitted.

Comparing FIGS. 13 and 14 with ach other, it is understood that a through hole PH corresponding to the through hole MH located on the central portion of the corresponding area $MD_{ij}$ of the master pattern is not present on the corresponding position of the object pattern divisional area $PD_{ij}$. In other words, the through hole PH to be present is not formed, to result in the "unperforated defect".

This unperforated defect is inspected by determining whether or not the corresponding through hole PH is present with respect to each through hole MH in the corresponding area $MD_{ij}$ of the master pattern.

More specifically, it is determined that no through hole PH corresponding to the through hole MH is present in the object pattern divisional area $PD_{ij}$ when no centroidal position G of a through hole PH as to object data is present in a circular area BR having a constant distance (i.e., radius) b from the centroidal position $G_M$ of the through hole MH present on a normal position, as shown in FIG. 15. FIG. 15 shows only the circular area BR as to the central through hole MH.

When the through hole PH corresponding to the through hole MH is present, i.e., when the correspondence between the through holes MH and PH is obtained, the aforementioned "misregistration defect" and the "hole diameter defect" as well as the "chip clogging defect" and the "hole deformation defect" described later can be detected by comparing each through hole MH with the through hole PH corresponding thereto.

Detection of the "excess hole defect" is now described with reference to FIGS. 14, 16 and 17. FIG. 16 illustrates another exemplary object pattern divisional area $PD_{ij}$ extracted as the defect candidate area. It is assumed that the corresponding area $MD_{ij}$ of the master pattern shown in FIG. 14 corresponds to this object pattern divisional area $PD_{ij}$. FIG. 17 illustrates the areas $PD_{ij}$ and $MD_{ij}$ in positional correspondence to each other. In FIG. 17, solid circles express through holes MH in the corresponding area $MD_{ij}$ of the master pattern, while crosses express centroidal positions G of through holes PH in the object pattern divisional area $PD_{ij}$. Referring to FIG. 17, centroidal positions $G_M$ of the through holes MH and circles showing the contours of the through holes PH are omitted.

Comparing FIGS. 14 and 16 with each other, it is understood that no through hole MH corresponding to a through hole PH present at the lower right of the object pattern divisional area $PD_{ij}$ is present on the corresponding position of the corresponding area $MD_{ij}$ of the master pattern. In other words, this through hole PH is excessively formed as the "excess hole defect".

In order to detect this "excess hole defect", whether or not the corresponding through hole MH is present is determined as to each through hole PH present in the object pattern divisional area $PD_{ij}$, contrarily to the case of the aforementioned "unperforated defect".

The determination is made with reference to the centroidal position G of each through hole PH in the object pattern divisional area $PD_{ij}$. More specifically, as shown in FIG. 17, when no centroidal position $G_M$ of the through hole MH as to master data corresponding to the centroidal position G of the through hole PH is present in a circular area BR having a constant distance (i.e., radius) b from the centroidal position G of the through hole PH, determination on a defect is made on the assumption that no through hole MH corresponding to the through hole PH is present in the corresponding area of the master pattern, i.e., an unwanted through hole (i.e., an excess through hole) PH is formed. FIG. 17 shows only the circular area BR as to the right lower through hole PH.

Figure 18A:
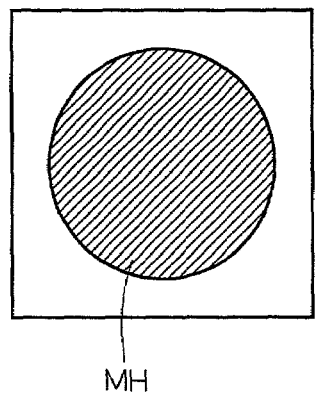
FIGS. 18A and 18B illustrate a "chip clogging defect"
Figure 18B:
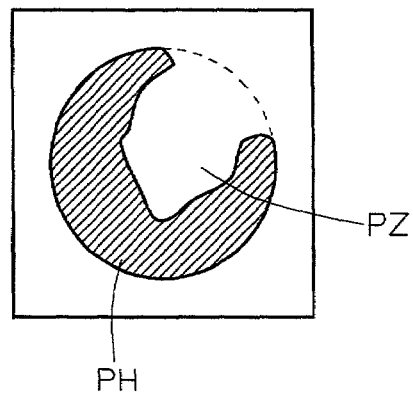
Figure 19A:
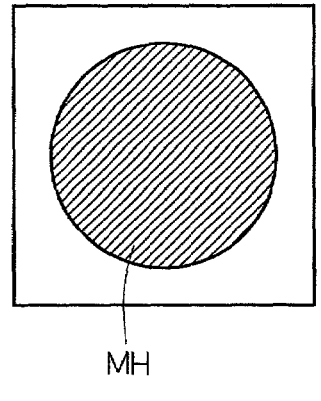
FIGS. 19A and 19B illustrate a "hole deformation defect"
Figure 19B:
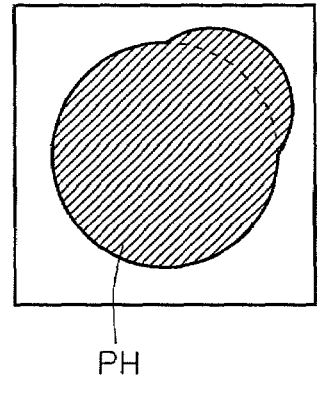

Detection of the "chip clogging defect" and the "hole deformation defect" is described with reference to FIGS. 18A, 18B, 19A and 19B. FIG. 18B illustrates the "chip clogging defect" of a through hole PH partially clogged with a chip PZ, and FIG. 19B illustrates the "hole deformation defect" of a through hole PH having a deformed shape. FIGS. 18A and 19A illustrate ideal through holes MH.

The chip clogging defect and the hole deformation defect are determined on the basis of difference between the diameters D of the through holes PH and MH. In other words, these defects can be detected as kinds of the aforementioned "hole diameter defect". If the through hole PH is partially clogged with the chip PZ, the image area (square measure) R thereof is reduced and hence the diameter D obtained in the aforementioned manner is also reduced. Utilizing this nature, the chip clogging defect is detected. This also applies to the through hole PH deformed as shown in FIG. 19B. The diameter D obtained in the aforementioned manner is varied with change of the image area R also in this case. Utilizing this nature, the hole deformation is also detected.

The through hole inspection apparatus 1 performs defect detection as to the through holes in the aforementioned manner.

<C. Effects of the Embodiment>

Also when the inspected object has a registration error resulting from misregistration or distortion, the through hole inspection apparatus 1 according to the aforementioned embodiment can absorb the registration error and quickly perform precise pattern defect detection by carrying out the aforementioned first-stage operation.

Further, an area subjected to the subsequent second-stage operation can be selected as a defect candidate area from a plurality of object pattern divisional areas by executing the first-stage operation (step SP30).

Thereafter the feature quantity is extracted as to the through hole through the second-stage operation (steps SP40 and SP50) for performing defect determination, whereby the defect of the through hole can be more correctly determined. The second-stage operation enabling correct defect detection generally requires a longer processing time as compared with the first-stage operation. Therefore, efficient defect detection can be performed by reducing the number of the object pattern divisional areas $PD_{ij}$ to be subjected to the second-stage operation through the first-stage operation.

In particular, a plurality of types of defects can be detected every type by detecting various types of defects in comparison with allowances responsive to the types of the defects in the second-stage operation. Further, it is also possible to improve objectivity of the defect detection by comparing the defects with the respective allowances as to hole positions and hole diameters and digitizing (evaluating) the degrees of the defects.

<D. Others>

The through hole inspection apparatus 1 according to the aforementioned embodiment scans the overall patterns with the defect inspection windows having the size corresponding to a plurality of pixels for comparing the object pattern divisional area and the master pattern divisional area group corresponding thereto for determining pattern mismatch when the values of all corresponding pixels of the patterns included in the windows mismatch with each other on at least one scanning position.

However, the present invention is not restricted to this but pattern mismatch may alternatively be determined when the values of at least a prescribed number of corresponding pixels included in the windows mismatch with each other on at least one scanning positions, through scanning with defect inspection windows having a size corresponding to a plurality of pixels.

In other words, pattern mismatch may be determined not when all pixels in inspection windows W having a defect size corresponding to a plurality of pixels (assumed to be 2 by 2 pixels here) mismatch with each other but only when at least a prescribed number of pixels (i.e., at least a prescribed ratio of pixels) in the inspection windows W having a size, larger than a defect pixel size, corresponding to a plurality of pixels mismatch with each other. When the inspection windows W are formed by 4 by 4 pixels, i.e., 16 pixels in total, for example, pattern mismatch may be determined when about 10 pixels mismatch with each other among the 16 pixels.

While the object pattern data is so divided that each divisional area $PD_{ij}$ includes a plurality of through holes H in the aforementioned embodiment, the present invention is not restricted to this. For example, the size of each divisional area $PD_{ij}$ may alternatively be so set that each divisional area $PD_{ij}$ includes a single through hole at the maximum. More specifically, the size of each divisional area $PD_{ij}$ may be set as a prescribed value exceeding the diameter D (theoretical value) of the through hole H to be inspected (the maximum value when a plurality of diameters are present) and not more than the minimum value of the distance between the centroidal positions of the plurality of through holes H. The range of the defect candidate areas to be subjected to the second-stage operation can be further limited by finely dividing the object pattern data.

While the diameter D of each through hole H is calculated from the area R thereof in the aforementioned embodiment, the present invention is not restricted to this. The diameter D of the through hole H can alternatively be obtained as the length of a side of the minimum square in contact with the through hole H, for example. Further alternatively, the diameter D of the through hole H can be obtained as the difference between the positions of two pixels most separated from the centroidal position of the through hole H along the direction X (or Y) in the through hole H.

Figure 20:
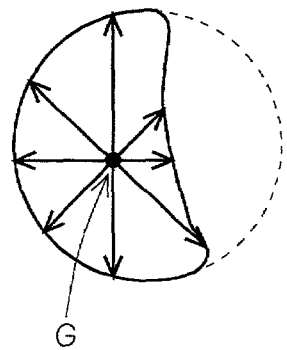
FIG. 20 illustrates another method of detecting the chip clogging defect and the hole deformation defect.

In this case, however, the diameter D is not a value obtained on the basis of the area R. Therefore, the "chip clogging defect" and the "hole deformation defect" are preferably detected by another method. As shown in FIG. 20, for example, the lengths of arms extending toward eight directions from a centroidal position G may be obtained for determining the defects by detecting whether or not the lengths of these arms are equal to each other.

While the above embodiment has been described with reference to the hole inspection apparatus (the through hole inspection apparatus 1) inspecting the "holes as through holes", the present invention is not restricted to this but is also applicable to a hole inspection apparatus inspecting general "holes" formed in an inspected object. For example, the present invention is also applicable to a hole inspection apparatus inspecting "holes indented to intermediate portions along the thickness of the inspected object" such as holes (bride via holes or laser via holes) passing through at least one layer but not all layers of a multilayer substrate, for example. In order to inspect the bride via holes, an epi-illumination system may be employed for illumination for picking up an image of a pattern by receiving light reflected by the inspected object with an image pickup device such as a CCD. In this case, a technique similar to the above may be applied to "hole information" as to a wider concept of "holes" in place of the "hole information" as to through holes.

While the inspected object is formed by the plate-type printed board 4 in the aforementioned embodiment, the present invention is not restricted to this but is also applicable to an inspected object such as a web printed substrate, for example.

While the invention has been shown and described in detail, the foregoing description is in all aspects illustrative and not restrictive. It is therefore understood that numerous modifications and variations can be devised without departing from the scope of the invention.

What is claimed is:

1. An apparatus for inspecting a plurality of holes formed in an inspected object, comprising:

image pickup means for picking up an image of said inspected object having said plurality of holes for acquiring object pattern data;

storage means for storing master pattern data expressing an ideal state of said inspected object;

area division means for dividing said object pattern data into a plurality of object pattern divisional areas having a prescribed size;

defect candidate area extraction means for comparing each said object pattern divisional area with master pattern data corresponding to said each object pattern divisional area thereby determining whether or not each said object pattern divisional area is a defect candidate and extracting a defect candidate area from said plurality of object pattern divisional areas;

first acquisition means for obtaining first hole information as to holes present in said object pattern divisional area extracted as said defect candidate area from said plurality of object pattern divisional areas;

second acquisition means for obtaining second hole information as to holes present in an area of said master pattern data corresponding to said object pattern divisional area extracted as said defect candidate area; and defect determination means for comparing said first hole information and said second hole information with each other for determining whether or not each said hole is defective on the basis of a result of comparison.

2. The apparatus according to claim 1, wherein said defect candidate area extraction means comprises
i) means for selecting an objective area among said plurality of object pattern divisional areas,
ii) means for determining a part of said master pattern area corresponding to said objective area to determine a first reference area,
iii) shifting means for shifting said first reference area to respective directions on a two-dimensional plane pixel by pixel within a predetermined pixel number range to obtain a plurality of second reference areas, respectively,
iv) comparing means for comparing said objective area with said plurality of second reference areas, said comparing means comprising
means for scanning said objective area and said plurality of second reference areas with a defect inspection window having a size corresponding to a plurality of pixels, and
means for counting inconsistent pixels at which said objective area has pixel values different from at least one second reference areas for each scanning position of said defect inspection window, to determine a pattern mismatch when a counted number of said inconsistent pixels are more than a predetermined threshold number, and
v) determination means for determining said objective area as said defect candidate area only when said pattern mismatch is found for all of said plurality of second reference areas.

3. The apparatus according to claim 2, wherein the size of said object pattern divisional areas is so set as to include one hole in each said object pattern divisional area at the maximum.

4. The apparatus according to claim 3, wherein each of said first hole information and said second hole information includes the centroidal position of said holes, and
said defect determination means calculates the shift amount between the centroidal position included in said first hole information and the centroidal position included in said second hole information and compares said shift amount with a prescribed allowance thereby determining whether or not each said hole is defective.

5. The apparatus according to claim 3, wherein each of said first hole information and said second hole information includes the area of said holes, and
said defect determination means calculates the shift amount between the area included in said first hole information and the area included in said second hole information and compares said shift amount with a prescribed allowance thereby determining whether or not each said hole is defective.

6. The apparatus according to claim 1, wherein the size of said object pattern divisional areas is so set as to include one hole in each said object pattern divisional area at the maximum.

7. The apparatus according to claim 1, wherein each of said first hole information and said second hole information includes the centroidal position of said holes, and
said defect determination means calculates the shift amount between the centroidal position included in said first hole information and the centroidal position included in said second hole information and compares said shift amount with a prescribed allowance thereby determining whether or not each said hole is defective.

8. The apparatus according to claim 1, wherein each of said first hole information and said second hole information includes the area of said holes, and
said defect determination means calculates the shift amount between the area included in said first hole information and the area included in said second hole information and compares said shift amount with a prescribed allowance thereby determining whether or not each said hole is defective.

9. The apparatus according to claim 2, wherein each of said first hole information and said second hole information includes the centroidal position of said holes, and
said defect determination means calculates the shift amount between the centroidal position included in said first hole information and the centroidal position included in said second hole information and compares said shift amount with a prescribed allowance thereby determining whether or not each said hole is defective.

10. The apparatus according to claim 2, wherein each of said first hole information and said second hole information includes the area of said holes, and
said defect determination means calculates the shift amount between the area included in said first hole information and the area included in said second hole information and compares said shift amount with a prescribed allowance thereby determining whether or not each said hole is defective.

11. A method of inspecting a plurality of holes formed in an inspected object, including steps of:
a) picking up an image of said inspected object having said plurality of holes and acquiring object pattern data;
b) storing master pattern data expressing an ideal state of said inspected object;
c) dividing said object pattern data into a plurality of object pattern divisional areas having a prescribed size;
d) comparing each said object pattern divisional area with master pattern data corresponding to said each object pattern divisional area thereby determining whether or not each said object pattern divisional area is a defect candidate and extracting a defect candidate area from said plurality of object pattern divisional areas;
e) obtaining first hole information as to holes present in said object pattern divisional area extracted from said plurality of object pattern divisional areas as said defect candidate area;
f) obtaining second hole information as to holes present in an area of said master pattern data corresponding to said object pattern divisional area extracted as said defect candidate area; and g) comparing said first hole information and said second hole information with each other for determining whether or not each said hole is defective on the basis of a result of comparison.

12. The method according to claim 11, wherein
said step (d) comprises the steps of
d-1) selecting an objective area among said plurality of object pattern divisional areas,
d-2) determining a part of said master pattern area corresponding to said objective area to determine a first reference area,
d-3) shifting said first reference area to respective directions on a two-dimensional plane pixel by pixel within a predetermined pixel number range to obtain a plurality of second reference areas, respectively,
d-4) comparing said objective area with said plurality of second reference areas, comprising the steps of
scanning said objective area and said plurality of second reference areas with a defect inspection window having a size corresponding to a plurality of pixels, and
counting inconsistent pixels at which said objective area has pixel values different from at least one second reference areas for each scanning position of said defect inspection window, to determine a pattern mismatch when a counted number of said inconsistent pixels are more than a predetermined threshold number, and
d-5) determining said objective area as said defect candidate area only when said pattern mismatch is found for all of said plurality of second reference areas.

13. The method according to claim 12, wherein
the size of said object pattern divisional areas is so set as to include one hole in each said object pattern divisional area at the maximum.

14. The method according to claim 13, wherein
each of said first hole information and said second hole information includes the centroidal position of said holes,
the shift amount between the centroidal position included in said first hole information and the centroidal position included in said second hole information is calculated and said shift amount is compared with a prescribed allowance thereby determining whether or not each said hole is defective in said step (g).

15. The method according to claim 13, wherein
each of said first hole information and said second hole information includes the area of said holes,
the shift amount between the area included in said first hole information and the area included in said second hole information is calculated and said shift amount is compared with a prescribed allowance thereby determining whether or not each said hole is defective in said step (g).

16. The method according to claim 11, wherein
the size of said object pattern divisional areas is so set as to include one hole in each said object pattern divisional area at the maximum.

17. The method according to claim 11, wherein
each of said first hole information and said second hole information includes the centroidal position of said holes,
the shift amount between the centroidal position included in said first hole information and the centroidal position included in said second hole information is calculated and said shift amount is compared with a prescribed allowance thereby determining whether or not each said hole is defective in said step (g).

18. The method according to claim 11, wherein
each of said first hole information and said second hole information includes the area of said holes,
the shift amount between the area included in said first hole information and the area included in said second hole information is calculated and said shift amount is compared with a prescribed allowance thereby determining whether or not each said hole is defective in said step (g).

19. The method according to claim 12, wherein
each of said first hole information and said second hole information includes the centroidal position of said holes,
the shift amount between the centroidal position included in said first hole information and the centroidal position included in said second hole information is calculated and said shift amount is compared with a prescribed allowance thereby determining whether or not each said hole is defective in said step (g).

20. The method according to claim 12, wherein
each of said first hole information and said second hole information includes the area of said holes,
the shift amount between the area included in said first hole information and the area included in said second hole information is calculated and said shift amount is compared with a prescribed allowance thereby determining whether or not each said hole is defective in said step (g).

* * * * *